United States Patent
Rappaport et al.

(10) Patent No.: US 11,529,065 B2
(45) Date of Patent: Dec. 20, 2022

(54) METHODS AND DEVICES OF CARDIAC TISSUE MONITORING AND ANALYSIS

(71) Applicant: Sensible Medical Innovations Ltd., Netanya (IL)

(72) Inventors: Dan Rappaport, Tel-Aviv (IL); Amir Saroka, Herzlia (IL); Shlomi Bergida, Ein Sarid (IL); Ilan Kochba, Modiln (IL); Nadav Mizrahi, Tel-Aviv (IL)

(73) Assignee: Sensible Medical Innovations Ltd., Netanya (IL)

( * ) Notice: Subject to any disclaimer, the term of this patent is extended or adjusted under 35 U.S.C. 154(b) by 210 days.

(21) Appl. No.: 16/888,921

(22) Filed: Jun. 1, 2020

(65) Prior Publication Data

US 2020/0289018 A1    Sep. 17, 2020

Related U.S. Application Data

(63) Continuation of application No. 12/544,314, filed on Aug. 20, 2009, now Pat. No. 10,667,715.

(60) Provisional application No. 61/090,356, filed on Aug. 20, 2008.

(51) Int. Cl.
| | |
|---|---|
| *A61B 5/05* | (2021.01) |
| *A61B 5/0507* | (2021.01) |
| *A61B 5/25* | (2021.01) |
| *A61B 5/366* | (2021.01) |

(52) U.S. Cl.
CPC .............. *A61B 5/05* (2013.01); *A61B 5/0507* (2013.01); *A61B 5/25* (2021.01); *A61B 5/366* (2021.01)

(58) Field of Classification Search
CPC ......... A61B 5/05; A61B 5/0507; A61B 5/366; A61B 5/25
See application file for complete search history.

(56) References Cited

U.S. PATENT DOCUMENTS

| | | |
|---|---|---|
| 3,534,727 A | 10/1970 | Roman |
| 4,016,868 A | 4/1977 | Allison |
| 4,240,445 A | 12/1980 | Iskander et al. |
| 4,279,257 A | 7/1981 | Hochstein |
| 4,381,510 A | 4/1983 | Wren |

(Continued)

FOREIGN PATENT DOCUMENTS

| | | |
|---|---|---|
| CA | 2898342 | 7/2014 |
| EP | 0694282 | 1/1996 |

(Continued)

OTHER PUBLICATIONS

Advisory Action Before the Filing of an Appeal Brief dated Mar. 2, 2016 From the US Patent and Trademark Office Re. U.S. Appl. No. 12/676,381.

(Continued)

*Primary Examiner* — Joel F Brutus

(57) ABSTRACT

A method for monitoring at least one cardiac tissue. The method comprises a) intercepting a plurality of reflections of an electromagnetic (EM) radiation reflected from at least one cardiac tissue of a patient in a plurality of EM radiation sessions, b) computing a mechanical tracing indicative of at least one mechanical property of said at least one cardiac tissue according to said plurality of reflections, c) analyzing said mechanical tracing so as to detect a presence or an absence of a physiological condition, and d) outputting said analysis.

20 Claims, 7 Drawing Sheets

(56) References Cited

U.S. PATENT DOCUMENTS

| | | |
|---|---|---|
| 4,488,559 A | 12/1984 | Iskander |
| 4,572,197 A | 2/1986 | Moore et al. |
| 4,580,572 A | 4/1986 | Granek et al. |
| 4,647,281 A | 3/1987 | Carr |
| 4,676,252 A | 6/1987 | Trautman et al. |
| 4,690,149 A | 9/1987 | Ko |
| 4,877,034 A | 10/1989 | Atkins et al. |
| 4,920,969 A | 5/1990 | Suzuki et al. |
| 4,926,868 A | 5/1990 | Larsen |
| 4,958,638 A | 9/1990 | Sharpe et al. |
| 4,991,585 A | 2/1991 | Mawhinney |
| 5,002,060 A | 3/1991 | Nedivi |
| 5,078,134 A | 1/1992 | Heilman et al. |
| 5,132,623 A | 7/1992 | De et al. |
| 5,282,840 A | 2/1994 | Hudrlik |
| 5,334,141 A | 8/1994 | Carr et al. |
| 5,363,050 A | 11/1994 | Guo et al. |
| 5,394,882 A | 3/1995 | Mawhinney |
| 5,479,120 A | 12/1995 | McEwan |
| 5,517,198 A | 5/1996 | McEwan |
| 5,523,760 A | 6/1996 | McEwan |
| 5,563,605 A | 10/1996 | McEwan |
| 5,573,012 A | 11/1996 | McEwan |
| 5,576,627 A | 11/1996 | McEwan |
| 5,604,531 A | 2/1997 | Iddan et al. |
| 5,728,143 A | 3/1998 | Gough et al. |
| 5,738,102 A | 4/1998 | Lemelson |
| 5,749,369 A | 5/1998 | Rabinovich et al. |
| 5,766,208 A | 6/1998 | McEwan |
| 5,804,921 A | 9/1998 | McEwan et al. |
| 5,805,110 A | 9/1998 | McEwan |
| 5,807,257 A | 9/1998 | Bridges |
| 5,829,437 A | 11/1998 | Bridges |
| 5,833,711 A | 11/1998 | Schneider, Sr. |
| 5,861,019 A | 1/1999 | Sun et al. |
| 5,876,353 A | 3/1999 | Riff |
| 5,883,591 A | 3/1999 | McEwan |
| 5,947,910 A | 9/1999 | Zimmet |
| 5,957,861 A | 9/1999 | Combs et al. |
| 5,964,703 A | 10/1999 | Goodman et al. |
| 5,995,863 A | 11/1999 | Farace et al. |
| 6,015,386 A | 1/2000 | Kensey et al. |
| 6,026,173 A | 2/2000 | Svenson et al. |
| 6,061,589 A | 5/2000 | Bridges et al. |
| 6,064,903 A | 5/2000 | Riechers et al. |
| 6,111,415 A | 8/2000 | Moshe |
| 6,169,925 B1 | 1/2001 | Villaseca et al. |
| 6,211,663 B1 | 4/2001 | Moulthrop et al. |
| 6,233,479 B1 | 5/2001 | Haddad et al. |
| 6,236,889 B1 | 5/2001 | Soykan et al. |
| 6,281,843 B1 | 8/2001 | Evtioushkine et al. |
| 6,330,479 B1 | 12/2001 | Stauffer |
| 6,332,087 B1 | 12/2001 | Svenson et al. |
| 6,332,091 B1 | 12/2001 | Burns et al. |
| 6,351,246 B1 | 2/2002 | McCorkle |
| 6,417,797 B1 | 7/2002 | Cousins et al. |
| 6,425,878 B1 | 7/2002 | Shekalim |
| 6,459,931 B1 | 10/2002 | Hirschman |
| 6,484,047 B1 | 11/2002 | Vilsmeier |
| 6,487,428 B1 | 11/2002 | Culver et al. |
| 6,488,677 B1 | 12/2002 | Bowman et al. |
| 6,494,829 B1 | 12/2002 | New, Jr. et al. |
| 6,496,711 B1 | 12/2002 | Athan et al. |
| 6,512,949 B1 | 1/2003 | Combs et al. |
| 6,551,252 B2 | 4/2003 | Sackner et al. |
| 6,574,510 B2 | 6/2003 | Von Arx et al. |
| 6,577,709 B2 | 6/2003 | Tarr |
| 6,590,545 B2 | 7/2003 | McCorkle |
| 6,675,045 B2 | 1/2004 | Mass et al. |
| 6,682,480 B1 | 1/2004 | Habib et al. |
| 6,687,523 B1 | 2/2004 | Jayaramen et al. |
| 6,746,404 B2 | 6/2004 | Schwartz |
| 6,766,201 B2 | 7/2004 | Von Arx et al. |
| 6,770,070 B1 | 8/2004 | Balbierz |
| 6,783,499 B2 | 8/2004 | Schwartz |
| 6,788,262 B1 | 9/2004 | Adams et al. |
| 6,802,811 B1 | 10/2004 | Slepian |
| 6,809,701 B2 | 10/2004 | Amundson et al. |
| 6,849,046 B1 | 2/2005 | Eyal-Bickels et al. |
| 6,909,397 B1 | 6/2005 | Greneker III et al. |
| 6,917,833 B2 | 7/2005 | Denker et al. |
| 6,954,673 B2 | 10/2005 | Von Arx et al. |
| 6,972,725 B1 | 12/2005 | Adams |
| 7,006,856 B2 | 2/2006 | Baker, Jr. et al. |
| 7,024,248 B2 | 4/2006 | Penner et al. |
| 7,047,058 B1 | 5/2006 | Dvorsky et al. |
| 7,072,718 B2 | 7/2006 | Von Arx et al. |
| 7,077,810 B2 | 7/2006 | Lange et al. |
| 7,110,823 B2 | 9/2006 | Whitehurst et al. |
| 7,116,276 B2 | 10/2006 | Lee |
| 7,122,012 B2 | 10/2006 | Bouton et al. |
| 7,135,871 B1 | 11/2006 | Pelletier |
| 7,229,415 B2 | 6/2007 | Schwartz |
| 7,228,047 B1 | 7/2007 | Szilagyi et al. |
| 7,315,170 B2 | 1/2008 | Sakayori |
| 7,316,658 B2 | 1/2008 | Gagne |
| 7,330,034 B1 | 2/2008 | Pelletier et al. |
| 7,387,610 B2 | 6/2008 | Stahmann et al. |
| 7,445,605 B2 | 11/2008 | Overall et al. |
| 7,450,077 B2 | 11/2008 | Waterhouse et al. |
| 7,483,752 B2 | 1/2009 | Von Arx et al. |
| 7,561,908 B2 | 7/2009 | Glukhovsky et al. |
| 7,591,792 B2 | 9/2009 | Bouton |
| 7,613,522 B2 | 11/2009 | Christman et al. |
| 7,628,757 B1 | 12/2009 | Koh |
| 7,674,244 B2 | 3/2010 | Kalafut et al. |
| 7,686,762 B1 | 3/2010 | Najafi et al. |
| 7,725,150 B2 | 5/2010 | Tupin, Jr. et al. |
| 7,729,776 B2 | 6/2010 | Von Arx et al. |
| 7,736,309 B2 | 6/2010 | Miller et al. |
| 7,756,587 B2 | 7/2010 | Penner et al. |
| 7,825,667 B2 | 11/2010 | Fang et al. |
| 7,837,629 B2 | 11/2010 | Bardy |
| 7,844,341 B2 | 11/2010 | Von Arx et al. |
| 7,860,574 B2 | 12/2010 | Von Arx et al. |
| 7,872,613 B2 | 1/2011 | Keilman et al. |
| 8,032,199 B2 | 10/2011 | Linti et al. |
| 8,235,949 B2 | 8/2012 | Hack et al. |
| 10,506,943 B2 | 12/2019 | Kochba et al. |
| 2003/0036674 A1 | 2/2003 | Bouton |
| 2003/0036713 A1 | 2/2003 | Bouton et al. |
| 2003/0128808 A1 | 7/2003 | Kindlein et al. |
| 2004/0006279 A1 | 1/2004 | Arad (Abboud) |
| 2004/0073093 A1 | 4/2004 | Hatlestad |
| 2004/0148021 A1 | 7/2004 | Cartledge et al. |
| 2004/0186395 A1 | 9/2004 | Vastano |
| 2004/0249257 A1 | 12/2004 | Tupin, Jr. et al. |
| 2004/0249258 A1 | 12/2004 | Tupin, Jr. et al. |
| 2004/0254457 A1 | 12/2004 | Van der Weide |
| 2005/0065567 A1 | 3/2005 | Lee et al. |
| 2005/0107719 A1 | 5/2005 | Arad (Abboud) |
| 2005/0124908 A1 | 6/2005 | Belalcazar et al. |
| 2005/0149139 A1 | 7/2005 | Plicchi et al. |
| 2005/0171396 A1 | 8/2005 | Pankratov et al. |
| 2005/0177061 A1 | 8/2005 | Alanen et al. |
| 2006/0058606 A1 | 3/2006 | Davis et al. |
| 2006/0235289 A1 | 10/2006 | Wesselink et al. |
| 2006/0258952 A1 | 11/2006 | Stahmann et al. |
| 2006/0293609 A1 | 12/2006 | Stahmann et al. |
| 2007/0032749 A1* | 2/2007 | Overall ............ A61B 5/02444 600/595 |
| 2007/0066904 A1 | 3/2007 | Wiesmann et al. |
| 2007/0088221 A1 | 4/2007 | Stahmann |
| 2007/0123770 A1 | 5/2007 | Bouton et al. |
| 2007/0163584 A1 | 7/2007 | Bohm et al. |
| 2007/0197878 A1 | 8/2007 | Shklarski |
| 2007/0238914 A1 | 10/2007 | Royality et al. |
| 2008/0097530 A1 | 4/2008 | Muccio |
| 2008/0103440 A1 | 5/2008 | Ferren et al. |
| 2008/0200802 A1 | 8/2008 | Bhavaraju et al. |
| 2008/0200803 A1 | 8/2008 | Kwon et al. |
| 2008/0224688 A1 | 9/2008 | Rubinsky et al. |
| 2008/0269589 A1 | 10/2008 | Thijs et al. |
| 2008/0283290 A1 | 11/2008 | Niino et al. |

(56) References Cited

U.S. PATENT DOCUMENTS

| | | |
|---|---|---|
| 2008/0288028 A1 | 11/2008 | Larson et al. |
| 2009/0043223 A1 | 2/2009 | Zhang et al. |
| 2009/0149918 A1 | 6/2009 | Krulevitch et al. |
| 2009/0227882 A1 | 9/2009 | Foo |
| 2009/0228001 A1 | 9/2009 | Pacey |
| 2009/0228075 A1 | 9/2009 | Dion |
| 2009/0241972 A1 | 10/2009 | Keilman et al. |
| 2009/0248129 A1 | 10/2009 | Keilman et al. |
| 2010/0056907 A1 | 3/2010 | Rappaport et al. |
| 2010/0256462 A1 | 10/2010 | Rappaport et al. |
| 2011/0025295 A1 | 2/2011 | Saroka et al. |
| 2011/0319746 A1 | 12/2011 | Kochba et al. |
| 2013/0281800 A1 | 10/2013 | Saroka et al. |
| 2017/0156626 A1 | 6/2017 | Kochba et al. |
| 2020/0113475 A1 | 4/2020 | Kochba et al. |
| 2020/0178837 A1 | 6/2020 | Rappaport et al. |

FOREIGN PATENT DOCUMENTS

| | | |
|---|---|---|
| EP | 1600892 | 11/2005 |
| JP | 2004-528864 | 9/2004 |
| JP | 2005-531386 | 10/2005 |
| JP | 2005-334298 | 12/2005 |
| JP | 2007-509353 | 4/2007 |
| WO | WO 99/39728 | 8/1999 |
| WO | WO 00/71207 | 11/2000 |
| WO | WO 02/053228 | 7/2002 |
| WO | WO 03/009753 | 2/2003 |
| WO | WO 2004/004539 | 1/2004 |
| WO | WO 2005/043100 | 5/2005 |
| WO | WO 2005/074361 | 8/2005 |
| WO | WO 2005/094369 | 10/2005 |
| WO | WO 2007/010460 | 1/2007 |
| WO | WO 2007/055491 | 5/2007 |
| WO | WO 2008/002251 | 1/2008 |
| WO | WO 2008/122056 | 10/2008 |
| WO | WO 2009/031149 | 3/2009 |
| WO | WO 2009/031150 | 3/2009 |
| WO | WO 2011/141915 | 11/2011 |

OTHER PUBLICATIONS

Advisory Action Before the Filing of an Appeal Brief dated Jun. 6, 2013 From the US Patent and Trademark Office Re. U.S. Appl. No. 12/676,385.
Advisory Action Before the Filing of an Appeal Brief dated Mar. 18, 2015 From the US Patent and Trademark Office Re. U.S. Appl. No. 12/544,314.
Advisory Action Before the Filing of an Appeal Brief dated Oct. 21, 2015 From the US Patent and Trademark Office Re. U.S. Appl. No. 13/254,852.
Advisory Action Before the Filing of an Appeal Brief dated Apr. 22, 2014 From the US Patent and Trademark Office Re. U.S. Appl. No. 13/254,852.
Advisory Action Before the Filing of an Appeal Brief dated Jul. 25, 2019 From the US Patent and Trademark Office Re. U.S. Appl. No. 12/544,314. (3 pages).
Applicant-Initiated Interview Summary dated Jul. 2, 2013 From the US Patent and Trademark Office Re. U.S. Appl. No. 12/676,381.
Applicant-Initiated Interview Summary dated Feb. 5, 2019 From the US Patent and Trademark Office Re. U.S. Appl. No. 12/676,381. (4 pages).
Applicant-Initiated Interview Summary dated Dec. 11, 2013 From the US Patent and Trademark Office Re. U.S. Appl. No. 12/544,314.
Applicant-Initiated Interview Summary dated Jun. 13, 2013 From the US Patent and Trademark Office Re. U.S. Appl. No. 12/676,385.
Applicant-Initiated Interview Summary dated May 16, 2014 From the US Patent and Trademark Office Re. U.S. Appl. No. 13/254,852.
Applicant-Initiated Interview Summary dated Feb. 20, 2015 From the US Patent and Trademark Office Re. U.S. Appl. No. 13/254,852.

Communication Pursuant to Article 94(3) EPC dated Aug. 4, 2014 From the European Patent Office Re. Application No. 08808013.0.
Communication Pursuant to Article 94(3) EPC dated Sep. 27, 2013 From the European Patent Office Re. Application No. 08808013.0.
Communication Pursuant to Article 94(3) EPC dated Oct. 1, 2019 From the European Patent Office Re. Application No. 17020594.2. (3 Pages).
Communication Pursuant to Article 94(3) EPC dated May 6, 2013 From the European Patent Office Re. Application No. 10712583.3.
Communication Pursuant to Article 94(3) EPC dated May 11, 2020 From the European Patent Office Re. Application No. 17020594.2. (3 Pages).
Communication Pursuant to Article 94(3) EPC dated Apr. 16, 2015 From the European Patent Office Re. Application No. 10712583.3.
Communication Pursuant to Article 94(3) EPC dated Dec. 17, 2018 From the European Patent Office Re. Application No. 17153865.5. (6 Pages).
Communication Pursuant to Article 94(3) EPC dated May 18, 2018 From the European Patent Office Re. Application No. 17153865.5. (4 Pages).
Communication Pursuant to Article 94(3) EPC dated Feb. 19, 2016 From the European Patent Office Re. Application No. 08789867.2.
Communication Pursuant to Article 94(3) EPC dated Mar. 19, 2014 From the European Patent Office Re. Application No. 08789867.2.
Communication Pursuant to Article 94(3) EPC dated May 22, 2014 From the European Patent Office Re. Application No. 10712583.3.
Communication Pursuant to Article 94(3) EPC dated Apr. 29, 2015 From the European Patent Office Re. Application No. 08789867.2.
Communication Pursuant to Article 94(3) EPC dated Oct. 29, 2013 From the European Patent Office Re. Application No. 08789867.2.
Communication Pursuant to Article 94(3) EPC dated Sep. 30, 2019 From the European Patent Office Re. Application No. 17153865.5. (4 Pages).
European Search Report and the European Search Opinion dated Apr. 3, 2017 From the European Patent Office Re. Application No. 17153865.5. (7 Pages).
European Search Report and the European Search Opinion dated Sep. 20, 2018 From the European Patent Office Re. Application No. 17020594.2. (7 Pages).
Examiner-Initiated Interview Summary dated Feb. 4, 2016 From the US Patent and Trademark Office Re. U.S. Appl. No. 12/676,381.
International Preliminary Report on Patentability dated Sep. 15, 2011 From the International Bureau of WIPO Re. Application No. PCT/IL2010/000182.
International Preliminary Report on Patentability dated Mar. 18, 2010 From the International Bureau of WIPO Re. Application No. PCT/IL2008/001198.
International Preliminary Report on Patentability dated Mar. 18, 2010 From the International Bureau of WIPO Re. Application No. PCT/IL2008/001199.
International Search Report and the Written Opinion dated Jun. 15, 2010 From the International Searching Authority Re. Application No. PCT/IL2010/000182.
International Search Report dated Feb. 4, 2009 From the International Searching Authority Re. Application No. PCT/IL2008/001198.
International Search Report dated Jan. 23, 2009 From the International Searching Authority Re. Application No. PCT/IL2008/001199.
Interview Summary dated Jun. 8, 2017 From the US Patent and Trademark Office Re. U.S. Appl. No. 13/922,299. (3 pages).
Notice of Reason for Rejection dated Oct. 23, 2015 From the Japanese Patent Office Re. Application No. 2015-000023 and Its Translation Into Enghsh.
Notice of Reason for Rejection dated Jan. 31, 2014 From the Japanese Patent Office Re. Application No. 2010-523644 and Its Translation Into Enghsh.
Office Action dated Jun. 5, 2013 From the Israel Patent Office Re. Application No. 214973 and Its Translation Into English.
Office Action dated Dec. 14, 2015 From the Israel Patent Office Re. Application No. 239240 and Its Translation Into English.
Office Action dated Apr. 28, 2014 From the Israel Patent Office Re. Application No. 214973 and Its Translation Into English.

(56) References Cited

OTHER PUBLICATIONS

Official Action dated Jul. 1, 2014 From the US Patent and Trademark Office Re. U.S. Appl. No. 12/676,381.
Official Action dated Aug. 2, 2018 From the US Patent and Trademark Office Re. U.S. Appl. No. 12/676,381. (19 pages).
Official Action dated Oct. 2, 2015 From the US Patent and Trademark Office Re. U.S. Appl. No. 13/922,299.
Official Action dated Jan. 3, 2019 From the US Patent and Trademark Office Re. U.S. Appl. No. 12/676,381. (14 pages).
Official Action dated Nov. 3, 2014 From the US Patent and Trademark Office Re. U.S. Appl. No. 12/544,314.
Official Action dated Apr. 4, 2012 From the US Patent and Trademark Office Re. U.S. Appl. No. 12/676,385.
Official Action dated Apr. 4, 2018 From the US Patent and Trademark Office Re. U.S. Appl. No. 12/544,314. (22 pages).
Official Action dated Jun. 4, 2018 From the US Patent and Trademark Office Re. U.S. Appl. No. 15/436,902. (44 pages).
Official Action Dated Sep. 4, 2014 From the US Patent and Trademark Office Re. U.S. Appl. No. 13/254,852.
Official Action dated Jul. 5, 2013 From the US Patent and Trademark Office Re. U.S. Appl. No. 12/846,861.
Official Action dated Apr. 7, 2017 From the US Patent and Trademark Office Re. U.S. Appl. No. 15/436,902. (41 Pages).
Official Action dated May 7, 2015 From the US Patent and Trademark Office Re. U.S. Appl. No. 12/676,381.
Official Action dated Oct. 7, 2015 From the US Patent and Trademark Office Re. U.S. Appl. No. 12/676,381.
Official Action dated Feb. 8, 2013 From the US Patent and Trademark Office Re. U.S. Appl. No. 12/676,381.
Official Action dated Mar. 9, 2017 From the US Patent and Trademark Office Re. U.S. Appl. No. 13/922,299. (40 pages).
Official Action dated Aug. 10, 2017 From the US Patent and Trademark Office Re. U.S. Appl. No. 13/922,299. (26 pages).
Official Action dated Jun. 10, 2015 From the US Patent and Trademark Office Re. U.S. Appl. No. 13/254,852.
Official Action dated Apr. 11, 2016 From the US Patent and Trademark Office Re. U.S. Appl. No. 12/676,381.
Official Action dated Mar. 11, 2014 From the US Patent and Trademark Office Re. U.S. Appl. No. 12/544,314.
Official Action dated Oct. 11, 2013 From the US Patent and Trademark Office Re. U.S. Appl. No. 12/544,314.
Official Action dated Dec. 12, 2013 From the US Patent and Trademark Office Re. U.S. Appl. No. 13/254,852.
Official Action dated Jul. 13, 2016 From the US Patent and Trademark Office Re. U.S. Appl. No. 12/544,314.
Official Action dated Sep. 13, 2012 From the US Patent and Trademark Office Re. U.S. Appl. No. 12/676,381.
Official Action dated Mar. 14, 2016 From the US Patent and Trademark Office Re. U.S. Appl. No. 13/254,852.
Official Action dated Mar. 15, 2019 From the US Patent and Trademark Office Re. U.S. Appl. No. 12/544,314. (5 Pages).
Official Action dated Oct. 15, 2012 From the US Patent and Trademark Office Re. U.S. Appl. No. 12/846,861.
Official Action dated Apr. 16, 2019 From the US Patent and Trademark Office Re. U.S. Appl. No. 15/436,902. (27 pages).
Official Action dated Nov. 16, 2017 From the US Patent and Trademark Office Re. U.S. Appl. No. 15/436,902. (45 pages).
Official Action dated Dec. 19, 2012 From the US Patent and Trademark Office Re. U.S. Appl. No. 12/544,314.
Official Action dated Dec. 20, 2012 From the US Patent and Trademark Office Re. U.S. Appl. No. 12/676,385.
Official Action dated Aug. 21, 2019 From the US Patent and Trademark Office Re. U.S. Appl. No. 13/922,299. (35 pages).
Official Action dated Oct. 22, 2013 From the US Patent and Trademark Office Re. U.S. Appl. No. 12/676,381.
Official Action dated Mar. 25, 2013 From the US Patent and Trademark Office Re. U.S. Appl. No. 13/254,852.
Official Action dated May 25, 2016 From the US Patent and Trademark Office Re. U.S. Appl. No. 13/922,299.
Official Action dated May 25, 2017 From the US Patent and Trademark Office Re. U.S. Appl. No. 12/544,314. (33 pages).
Official Action dated Sep. 25, 2015 From the US Patent and Trademark Office Re. U.S. Appl. No. 12/544,314.
Official Action dated Feb. 26, 2014 From the US Patent and Trademark Office Re. U.S. Appl. No. 12/846,861.
Official Action dated Dec. 27, 2016 From the US Patent and Trademark Office Re. U.S. Appl. No. 12/676,381. (37 pages).
Official Action dated Dec. 28, 2017 From the US Patent and Trademark Office Re. U.S. Appl. No. 12/676,381. (23 pages).
Official Action dated Jun. 29, 2018 From the US Patent and Trademark Office Re. U.S. Appl. No. 13/922,299. (27 pages).
Restriction Official Action dated Jul. 2, 2015 From the US Patent and Trademark Office Re. U.S. Appl. No. 13/922,299.
Restriction Official Action dated Jun. 7, 2012 From the US Patent and Trademark Office Re. U.S. Appl. No. 12/544,314.
Summons to Attend Oral Proceedings Pursuant to Rule 115(1) EPC Dated Mar. 16, 2016 From the European Patent Office Re. Application No. 10712583.3.
Summons to Attend Oral Proceedings Pursuant to Rule 115(1) EPC Dated Dec. 23, 2016 From the European Patent Office Re. Application No. 08789867.2. (4 Pages).
Supplementary European Search Report and the European Search Opinion dated Feb. 13, 2013 From the European Patent Office Re. Application No. 08789867.2.
Supplementary European Search Report and the European Search Opinion dated Feb. 14, 2013 From the European Patent Office Re. Application No. 08808013.0.
Translation of Notice of Reason for Rejection dated Sep. 24, 2013 From the Japanese Patent Office Re. Application No. 2010-523644.
Translation of Reason for Rejection dated Jul. 29, 2016 From the Japanese Patent Office Re. Application No. 2015-000023.
Written Opinion dated Feb. 4, 2009 From the International Searching Authority Re. Application No. PCT/IL2008/001198.
Written Opinion dated Jan. 23, 2009 From the International Searching Authority Re. Application No. PCT/IL2008/001199.
Azevedo et al "Micropower Impulse Radar", Science & Technologies Review, 17-29, Feb. 1996.
Billich "Bio-Medical Sensing Using Ultra Wideband Communications and Radar Technology", PhD Proposal, Department of Information and Telecommunication Technology—University of Trento, Italy—Jan. 2006 (10 pages).
Fear et al. "Enhancing Breast Tumor Detection With Near-Field Imaging", IEEE Microwave Magazine, pp. 48-56, Mar. 2002.
Fear et al. "Microwaves for Breast Cancer Detection", IEEE Potentials, 22(1): 12-18, Feb. 25, 2003.
Gabriel "Compilation of the Dielectric Properties of Body Tissues at RF and Microwave Frequencies", Final Technical Report for the Period Sep. 15, 1993 to Dec. 14, 1994, p. 1-21, Jan. 1996.
Gentili et al "A Versatile Microwave Plethysmograph for the Monitoring of Physiological Parameters", IEEE Transactions on Biomedical Engineering 49(10) 1204-1210, Oct. 2002.
Hill-Rom "The Vest® Airway Clearance System. Information for Physicians", Hill-Rom, Retrieved From the Internet, 3 P., Nov. 24, 2011.
Iskander et al. A Microwave Method for Measuring Changes in Lung Water Content: Numerical Simulation, IEEE Transactions on Biomedical Engineering 28(12): 797-804, Dec. 1981.
Jafari et al. "Ultrawideband Radar Imagingn System for Biomedical Applications", Journal of Vacuum Science and Technology A: Vacuum, Surfaces, and Films, 24(3): 752-757, May/Jun. 2006.
Jiang et al. "Ultrasound-Guided Microwave Imaging of Breast Cancer: Tissue Phantom and Pilot Clinical Experiments", Medical Physics, 32(8): 2528-2535, Aug. 2005.
Juweid et al. "Positron-Emission Tomography and Assessment of Cancer Therapy", The New England Journal of Medicine, 354(5): 496-507, Feb. 2, 2006.
Kagawa et al. "Advanced Exercise Control Using Miniature ECG and 3D Acceleration Sensors", D&D Forum on Telemedicine Systems: Issues, design, Development and Standardization at Globecom 2008, New Orleans, Louisiana, USA, 23 P., Dec. 2, 2008.

(56) References Cited

OTHER PUBLICATIONS

Katzeff et al. "Exercise Stress Testing and an Electromechanical S Wace of the Electrocardiogram", South African Medical Journal, 49(27): 1088-1090, Jun. 28, 1975.
Kerckhoffs et al. "Homogeneity of Cardiac Contraction Despite Physiological Asynchrony of Depolarization: A Model Study", Annals of Biomedical Engineering, 31: 536-547, 2003.
Kramer et al. "Dielectric Measurement of Cerebral Water Content Using A Network Analyzer", Neurological Research, 14: 255-258, Jun. 1992.
Lee et al. "Noninvasive Tests in Patients With Stable Coronarv Artery Disease", The New England Journal of Medicine, 344(24): 1840-1845, Jun. 14, 2001.
Li et al. "An Overview of Ultra-Wideband Microwave Imaging Via Space-Time Beamforming for Early-Stage Breast-Cancer Detection", IEEE Antennas and Propagation Magazine, 47(1): 19-34, Feb. 2005.
McClelland et al. "A Continuous 40 Motion Model from Multiple Respiratory Cycles for Use in Lung Radiotherapy", Medical Physics, 33(9): 3348-3358, Sep. 2006.
Meaney et al. "Microwave Imaging for Neoadjuvant Chemotherapy Monitoring", First European Conference on Antennas and Propagation, EuCAP 2006, Nice, France, Nov. 6-10, 2006, p. 1-4, Nov. 2006.
Meaney et al. "Near-Field Microwave Imaging of Biologically-Based Materials Using A Monopole Transceiver System", IEEE Transactions on Microwave Theory and Techniques, 46(1): 31-45, Jan. 1998.
Nopp et al. "Dielectric Properties of Lung Tissue as a Function of Air Content", Physics in Medicine and Biology, 38(6): 699-716, Jun. 1993.
Panetta "A Mathematical Model of Periodically Pulsed Chemotherapy: Tumor Recurrence and Metastasis in a Competitive Environment", Bulletin of Methematical Biology, 58(3): 425-447, 1996.
Park et al. "An Ultra-Wearable, Wireless, Low Power ECG Monitoring System", Proceedings of the IEEE Biomedical Circuits and Systems Conference, BioCAS 2006, London, UK, p. 241-244, Nov. 29-Dec. 1, 2006.
Pedersen et al "An Investigation of the Use of Microwave Radiation for Pulmonary Diagnostics", IEEE Transactions on Biomedical Engineering, 23(5): 410-412, Sep. 1976.
Pierard et al. "Stress Testing in Valve Disease", Heart 93:766-772, 2007.
Schantz "Introduction to Ultra-Wideband Antennas", IEEE Conference, on Ultra-Wideband Systems and Technologies, in Brownsboro, AL, USA, on Nov. 16-19, 2003, p. 1-9, 2003.
Schiller "Noninvasive Monitoring of Tumors", The New England Journal of Medicine, 359(4): 418-420, Jul. 24, 2008.
Semenov et al. "Dielectrical Spectroscopy of Canine Myocardium During Acute Ischemia and Hypoxia at Frequency Spectrum From 100 kHz to 6 GHz", IEEE Transactions on Medical Imaging, XP011076314, 21(6): 703-707, Jun. 2002.
Semenov et al. "Three-Dimensional Microwave Tomography: Initial Experimental Imaging of Animals", IEEE Transactions on Biomedical Engineering. XP011007196, 49(1): 55-63, Jan. 2002. Abstract, p. 56, col. 1, Lines 6, 7.
Shea et al. "Contrast-Enhanced Microwave Imaging of Breast Tumors: A Computational Study Using 3D Realistic Numerical Phantoms", Inverse Problems, 26: 1-22, 2010.
Smiseth et al. "Regional Left Ventricular Electric and Mechanical Activation and Relaxation", JACC, Journal of the American College of Cardiology, 47(1): 173-174, Jan. 3, 2006.
Thornton "Optimization of Protocols for Computed Tomography Coronary Angiography", Supplement to Applied Radiology, p. 54-62, Jun. 2002.
Wikipedia "Electronic Packaging", Retrieved from wikipedia.org, 4 Pages, Published Online on Dec. 2006.
Winters et al. "Estimation of the Frequency-Dependent Average Dielectric Properties of Breast Tissue Using A Time-Domain Inverse Scattering Technique" IEEE Transactions on Antennas and Propagation, 54(11): 3517-3528, Nov. 2006.
Winters et al. "Three-Dimensional Microwave Breast Imaging: Dispersive Dielectric Properties Estimation Using Patient-Specific Basis Functions", IEEE Transactions on Medical Imaging, 28(7): 969-981, Jul. 2007.
Yamokoski et al "OptiVol® Fluid Status Monitoring With an Implantable Cardiac Device: A Heart Failure Management System. ", 4:(6) 775-780 (doi:10.1586/17434440.4.6.775), Nov. 2007.
Zhou et al. "On the Resolution of UWB Microwave Imaging of Tumors in Random Breast Tissue", IEEE International Symposium of the Antennas and Propagation Society, Jul. 3-8, 2005, 3A: 831-834, Jul. 2005.
Zito et al "Wearable System-On-A-Chip Pulse Radar Sensors for the Health Care: System Overview", 21st Conference on Advanced Information Networking and Applications Workshop (AINAW'07), University of Pisa, Italy—2007, IEEE.
Zlochiver et al "A Portable Bio-Impedance System for Monitoring Lung Resistivity", Medical Engineering & Physics, 29(1): 93-100, 2007.
Official Action dated Mar. 17, 2022 from US Patent and Trademark Office Re. U.S. Appl. No. 16/792,357. (26 pages).
Official Action dated Jun. 24, 2022 from US Patent and Trademark Office Re. U.S. Appl. No. 16/714,869. (47 pages).

\* cited by examiner

METHODS AND DEVICES OF CARDIAC TISSUE MONITORING AND ANALYSIS

RELATED APPLICATIONS

This application is a continuation of U.S. patent application Ser. No. 12/544,314 filed on Aug. 20, 2009, which claims the benefit of priority of U.S. Provisional Patent Application No. 61/090,356 filed on Aug. 20, 2008. The contents of the above applications are all incorporated by reference as if fully set forth herein in their entirety.

This application also incorporates by reference the disclosures of International PCT Patent Applications Nos. PCT/IL2008/001198 and/or PCT/IL2008/001199, both filed on Sep. 4, 2008.

FIELD AND BACKGROUND OF THE INVENTION

The present invention, in some embodiments thereof, relates to monitoring and, more particularly, but not exclusively, to using EM radiation for monitoring changes of a cardiac performance.

Medical instruments in which an echo of a pulse of EM radiation is used to detect and locate structures in the human body are known, see YOUNG, J. D et. al. Examination of video pulse radar systems as potential biological exploratory tools in LARSEN, L. E., and JACOBI, J. H. (Eds.): 'Medical applications of microwave imaging' (IEEE Press, New York, 1986), pp. 82-105, which is incorporated herein by reference. Such medical instruments includes microwave imaging devices, which may be referred to as tissue sensing adaptive radar (TSAR) or imaging and other medical devices for detecting and possibly imaging internal biological tissues. The use of electromagnetic waves eliminates the need to expose the tissues to ionizing radiation, as performed during X-ray imaging, and to obtain relatively large tissue contrasts according to their water content.

During the last years, various methods and devices have been developed for diagnosing intrabody tissues of ambulatory patients using electromagnetic (EM) radiation. For example, International Patent Application Number IL2008/001198, filed on Sep. 4, 2008, which is incorporated herein by reference, describes a wearable monitoring device for monitoring at least one biological parameter of an internal tissue of an ambulatory user. The wearable monitoring device comprises at least one transducer configured for EM radiation to the internal tissue and intercepting reflections of the EM radiation therefrom in a plurality of continuous or intermittent EM radiation sessions during at least 24 hours, a processing unit configured for analyzing respective reflections and identifying a change in the at least one biological parameter accordingly, a reporting unit configured for generating a report according to the change, and a housing for containing the at least one transducer, the reporting unit, and the processing unit, the housing being configured for being disposed on the body of the ambulatory user.

Using EM radar for cardiac biomechanics assessment is mentioned in E. M. Staderini, "UWB radars in medicine," IEEE Aerospace and Electronic Systems Magazine, vol. 17, no. 1, pp. 13-18, 2002, which the content thereof is incorporated herein by reference.

The most widespread system for the monitoring of the cardiac activity is the electrocardiograph (ECG). The information provided by ECG is related to heart electrical activity. With time, ECG data has become a useful tool in monitoring the health of an ambulatory patient's heart. A prominent type of ECG monitoring is Holter monitoring in which ECG data is acquired continuously over a 24 hour period. Data acquired by Holter monitoring is useful in identifying patients who are at risk of ventricular tachycadia. To date, it has been difficult to properly identify late potentials in the data acquired by Holter monitoring. Late potentials are low level electrical signals that cause late activation of the heart within its cycle. Such late potentials can cause premature contraction and, eventually, severe fibrillation. Such late potentials have been difficult to detect because they are of too low a level (i.e., approximately 5 microvolts) and too high a frequency (i.e., approximately 250 hertz) for detection by conventional Holter monitoring systems.

SUMMARY OF THE INVENTION

According to some embodiments of the present invention there is provided a method for monitoring at least one cardiac tissue. The method comprises a) intercepting a plurality of reflections of an electromagnetic (EM) radiation reflected from at least one cardiac tissue of a patient in a plurality of EM radiation sessions, b) computing a mechanical tracing indicative of at least one mechanical property of the at least one cardiac tissue according to the plurality of reflections, c) analyzing the mechanical tracing so as to detect a presence or an absence of a physiological condition, and d) outputting the analysis.

Optionally, the intercepting is performed during a period of at least 6 hours.

Optionally, the mechanical property comprises a member of a group consisting of motion velocity, motion acceleration, contractility, a length of a heart contraction and a pulsation.

Optionally, the analyzing comprises matching the mechanical tracing to a temporal model.

Optionally, the computing comprises calculating a velocity of the at least one cardiac tissue according to a local deviation between signals generated according to EM reflections in first and second periods.

Optionally, the method further comprises receiving a cardioelectric tracing captured during the intercepting and combining between the cardioelectric tracing and the mechanical tracing to compute at least one electromechanical property of the at least one cardiac tissue, and the analyzing being performed according to the at least one electromechanical property.

Optionally, the computing comprises registering the mechanical tracing according to a movement of at least one of the patient and an organ of the patient.

Optionally, the computing comprises adjusting the mechanical tracing according to a blood saturation level of the patient.

Optionally, the computing comprises adjusting the mechanical tracing according to a motion of an additional body tissue of the patient.

Optionally, the computing comprises registering the mechanical tracing according to a posture of the patient.

Optionally, the patient is an ambulatory patient.

Optionally, the intercepting is performed during a period of at least 24 hours.

Optionally, the physiological condition is a cardiac pathological condition.

Optionally, the outputting comprises presenting the physiological condition to the patient.

Optionally, the outputting comprises forwarding a notification indicative of the physiological condition to a remote medical center.

Optionally, the plurality of EM radiations are intermittently transmitted during a period selected according to at least one of an activity of the patient and a vital sign of the patient.

Optionally, the method further comprises performing the a)-c) for an additional cardiac tissue so as to compute an additional mechanical tracing of at least one mechanical property of the at least one cardiac tissue and matching between the mechanical tracing and the additional mechanical tracing to estimate a synchrony between a contractility of the at least one cardiac tissue and a contractility of the additional cardiac tissue.

According to some embodiments of the present invention there is provided a method for monitoring at least one cardiac tissue. The method comprises a) computing a mechanical tracing of at least one mechanical property of at least one cardiac tissue of a heart of a patient according to electromagnetic (EM) radiation reflected therefrom during a period, b) receiving a cardioelectric tracing generated by measuring an electrical activity of the heart during the period, c) calculating at least one electromechanical property of the heart according to a relationship between the mechanical tracing and the cardioelectric tracing, d) automatically analyzing the at least one electromechanical property so as to detect a presence or an absence of a physiological condition during the period, and e) outputting the analysis.

Optionally, the mechanical property comprises a length of a cardiac cycle of the heart and the cardioelectric tracing comprises a QT interval of a respective of the cardioelectric tracing, the at least one electromechanical property being a relationship between the length and the QT interval.

Optionally, the period lasts at least 6 hours.

Optionally, the mechanical property comprises a number of heart contractions per cardiac cycle.

Optionally, the mechanical property comprises an electromechanical delay between an electrical activation of the at least one cardiac tissue and a respective mechanical activation of the at least one cardiac tissue during at least one cardiac cycle.

Optionally, the calculating comprises temporally correlating between the mechanical tracing and the cardioelectric tracing.

Optionally, the mechanical property comprises a relationship between a mechanical onset and an electric onset during at least one cardiac cycle.

Optionally, the mechanical property comprises an efficacy of a pacemaker.

According to some embodiments of the present invention there is provided a wearable monitoring apparatus for monitoring at least one cardiac tissue. The wearable monitoring apparatus comprises at least one transducer configured for intercepting at least one reflection of electromagnetic (EM) radiation from at least one cardiac tissue of a heart of an ambulatory patient, a processing unit configured for generating a mechanical tracing of at least one mechanical property of the at least one cardiac tissue by analyzing the at least one reflection so as to allow the identifying of at least one physiological condition, an output unit configured for outputting the analysis, and a housing for containing the at least one transducer, the processing unit, and the output unit, the housing being configured for being disposed on the body of the ambulatory patient.

Optionally, the wearable monitoring apparatus further comprises an cardioelectric sensor for measuring at least one electrical signal from heart, the processing unit configured for computing an electrical tracing based on the at least on electrical signal, calculating at least one electromechanical property of the heart according to a relationship between the mechanical tracing and the cardioelectric tracing, and identifying the at least one physiological condition according to the at least one electromechanical property.

Optionally, the wearable monitoring apparatus further comprises the housing contains the cardioelectric sensor.

Optionally, the cardioelectric sensor having a plurality of leads; wherein at least one of the plurality of leads is configured for being separately disposed on the body.

Optionally, the wearable monitoring apparatus further comprises an additional sensor for measuring a vital sign of the ambulatory patient the processing unit configured for performing the identification according to the vital sign.

More optionally, the additional sensor is a member of a group consisting of: a temperature sensor, a blood pressure transducer, a fluid rate recording transducer, and an echocardiographic sensor.

Optionally, at least one transducer comprises a plurality of transducers each configured for intercepting the at least one reflection from a different position on the body of the patient, the processing unit being configured for generating a spatial motion vector of the heart by analyzing the at least one reflection from each the transducer and identifying the at least one physiological condition according to the spatial motion vector.

Optionally, the wearable monitoring apparatus further comprises an additional transducer mounted to intercept the additional reflection of EM radiation from an additional cardiac tissue, the processing unit being configured for generating an additional mechanical tracing of at least one mechanical property of the additional cardiac tissue and identifying a synchrony between the additional cardiac tissue and the cardiac tissue accordingly, the physiological condition being identified according to the synchrony.

According to some embodiments of the present invention there is provided a method for positioning a cardiac resynchronization therapy (CRT) leads. The method comprises a) computing a mechanical tracing of at least one mechanical property of at least one cardiac tissue of a heart according to at least one reflection of electromagnetic (EM) radiation therefrom and a cardioelectric tracing generated by measuring an electrical activity of the heart, b) placing at least one cardiac resynchronization therapy (CRT) lead in a first location on the surface of the heart, c) calculating at least one electromechanical property of the heart according to a relationship between the mechanical tracing and the cardioelectric tracing, d) estimating the efficacy of the at least one CRT lead in the first location according to the at least one electromechanical property, and e) repositioning or fixating the at least one CRT lead according to the estimating.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
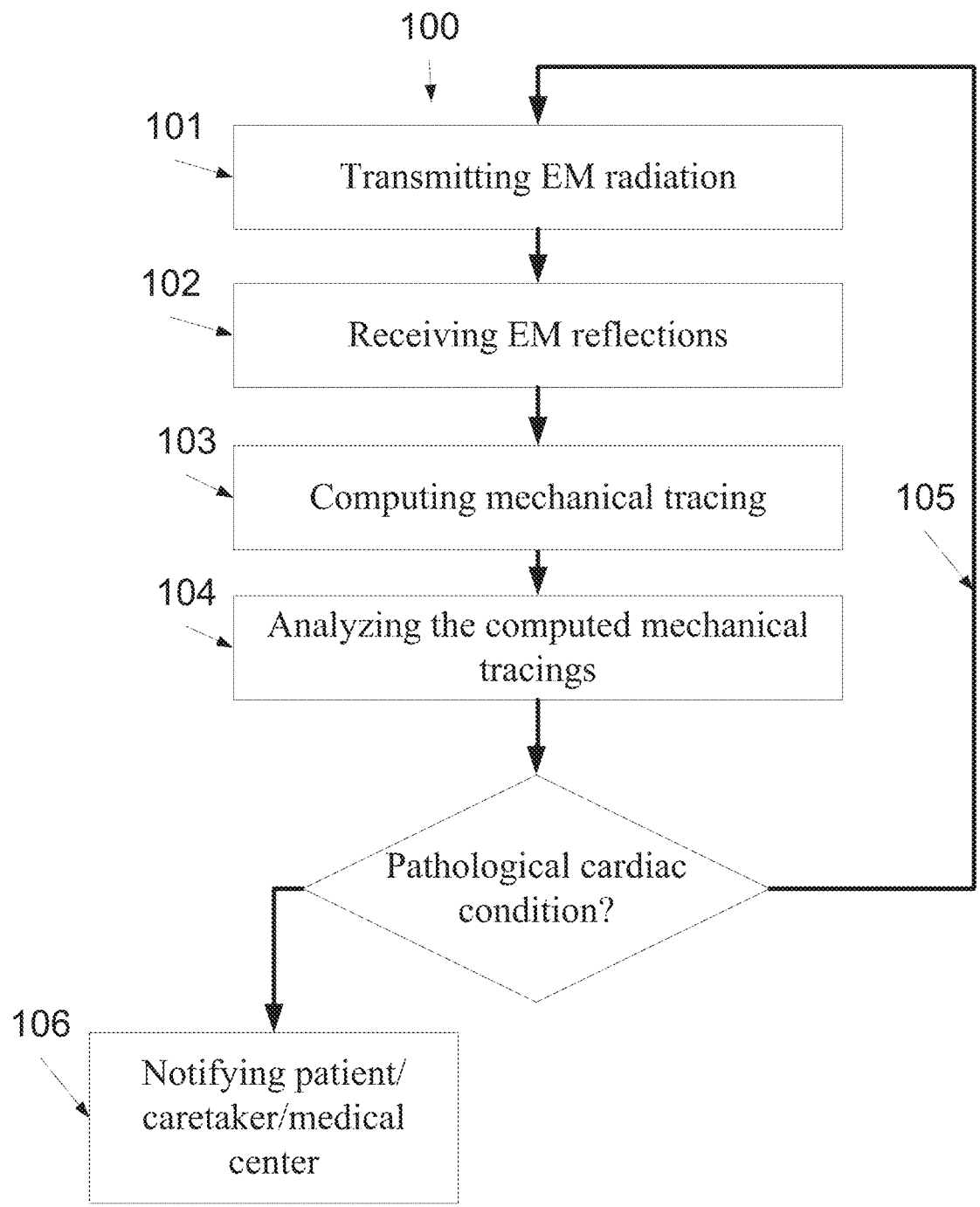
FIG. 1 is a flowchart of a method for monitoring one or more cardiac tissues of a patient during a monitoring period, according to some embodiments of the present invention.

The present invention, in some embodiments thereof, relates to monitoring and, more particularly, to using EM radiation for monitoring changes in cardiac performance.

According to some embodiments of the present invention there is provided a method and a device optionally wearable, for monitoring mechanical properties of one or more cardiac tissues by generating and analyzing mechanical tracings which are based on EM radiation reflected from the one or more cardiac tissues. The analysis allows detecting pathological conditions which may occur during the monitoring period, which is optionally of 6 hours or more, for example more than 24 hours. The device comprises one or more sensors or units that allow registering the mechanical tracings. In such a manner, the device may be used for monitoring ambulatory patients.

Optionally, the mechanical tracing documents the velocity of the motion of a certain cardiac motion during the monitoring period. Such a tracing may be used for estimating the acceleration of the cardiac tissue. Furthermore, the mechanical tracing may be used for detecting pathological conditions by detecting asynchronous contractions, multiple contractions per cardiac cycle, and asynchronous behavior in relation to other tissues. Optionally, the mechanical tracing documents the heart ejection fraction, and/or the contraction of the cardiac tissue during the monitoring period.

Optionally, the device includes a plurality of traducers that allows calculating a spatial motion vector of the one or more cardiac tissue. In such a manner, the mechanical tracing may be based on the spatial motion vector, providing data on the direction of contraction.

Optionally, the device includes a plurality of traducers that allows calculating a number of motion vectors, each of a different cardiac tissue. In such a manner, the synchrony of the motion of the different tissues may be evaluated.

According to some embodiments of the present invention there is provided a method and a device optionally wearable, for monitoring electromechanical properties of one or more cardiac tissues of a heart of a patient by generating and analyzing cardioelectric and mechanical tracings which are based on EM radiation reflected from the one or more cardiac tissues and an electric impulse from the heart. The analysis allows detecting pathological conditions which may occur during the monitoring period, which is optionally of 6 hours or more, for example more than 24 hours. Optionally, the wearable device integrates one or more leads of an ECG sensor that allows generating the cardioelectric tracing. Optionally, one or more leads are external to the wearable device and communicate connected thereto via wires.

Such a method and device allows monitoring, in real time electromechanical properties such as a delay between an electric activation of the myocardium and the contraction thereof, a delay between electric and mechanical onsets and various electromechanical relationship between the cardioelectric tracing and the cardiac cycle, for example an electromechanical relationship between a QT interval of the cardioelectric tracing and the length of a respective cardiac cycle. Optionally, the electromechanical properties include the electromechanical relationship between amplitude changes and cardiac mechanical function changes.

Optionally, the method is used for monitoring patients in certain risk groups, such as CHF patients, pacemaker recipients and the like According to some embodiments of the present invention there is provided method and device for a localization of pacemaker leads, such as cardiac resynchronization therapy (CRT) leads. The method and the device allow estimating the effect of the lead in different locations on the surface of the heart, allowing the surgeon to increase the efficacy of the CRT procedure.

For clarity, dielectric property of a material describes its interaction with EM fields; it is represented by a frequency dependent complex number describing the electrical permittivity and the conductivity of the material, as known in the art. Different human tissues are characterized by different dielectric coefficients. A dielectric coefficient of a cardiac tissue is affected by the dielectric coefficients of each of its components. As used herein a dielectric related property of a tissue means a property that is related to the dielectric coefficient thereof. Such a dielectric related property effects the reflection of electro-magnetic radiation that is transmitted on the related tissue, such example changes the attenuation of the reflection, changes the delay that is caused by the tissue, changes the phase of the reflection, and changes the dispersion of the radiation in the tissue.

A dielectric related property may refer to a region of a body and be affected by the dielectric properties of tissues in that region. Normal and/or abnormal processes may change the regional dielectric related property, due to a change of the composition of the volume. A specific region may change its dielectric related property due to tissue movement and a consequent change in the configuration of tissues within that volume. The dielectric related property of a certain biological tissue may change in repetitive and/or predictable patterns according to various biological processes. For example, periodic changes may be measured along with breathing and heart cycles.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart of a method 100 for monitoring one or more cardiac tissues of a patient during a monitoring period of more than 6 hours by analyzing mechanical properties of the cardiac tissues, according to some embodiments of the present invention. The monitoring may be performed when the patient is in a certain risk group, for example because of a medical treatment and/or procedure and/or a pathological factor and/or during a physiological activity, such as running, cycling and the like. As used herein, a mechanical property of a cardiac tissue means a motion pattern, a cardiac cycle pattern, a pulsation pattern, a relationship with additional data, such as the cardioelectric tracing, an outcome of a mechanical tracing which is based on the movement of a certain cardiac tissue and the like. For brevity cardiac tissue also means implants, such as stents and pacemaker leads. These elements have a substantial different dielectric coefficient resulting in strong EM reflection profile and therefore may facilitate the EM analysis process.

As shown at 101 and 102, the method is based on transmitting EM radiation to a cardiac tissue of an ambulatory user and intercepting at least one reflection of the EM radiation therefrom in a plurality of transmission sessions, optionally during a period of at least 6 hours, for example 24 hours, few days, a week, few weeks, a mouth and/or any intermediate or longer period. The EM radiation may be a RF signal based on continuous emission and\or pulse emission. The signal may be wide band or narrow band, or any composition of multiple signals, constant or varying in time. Varying in time may include frequency sweeping, frequency hopping and\or any other change of the spectral density over time. Wide band signal may be a composition of multiple narrow band signals, such as multi tone.

As shown at 103, the transmission—reception sessions, for brevity referred to herein as transmission sessions, allow computing one or more mechanical tracings of the cardiac tissue. Computing may comprise mathematical and signal processing optionally including utilization of model based processing and/or analysis using present and historical measured or calculated information. As used herein a mechanical tracing is data indicative of a mechanical property of the cardiac tissue during a period, for example the velocity, the acceleration, the heart ejection fraction, the contraction period, the duty cycle of the contraction the speed of contraction, and/or contraction of the cardiac tissue during a period. As used herein a cardiac tissue means the myocardium, the aorta, the pericardium, the atrial tissue, and/or any combination thereof, for example left and right ventricles.

The mechanical tracing may be indicative of the pattern of the motion of the cardiac tissue, the contractility of the cardiac tissue, the remodeling of the cardiac tissue and/or the pulsation of the cardiac tissue.

Figure 2:
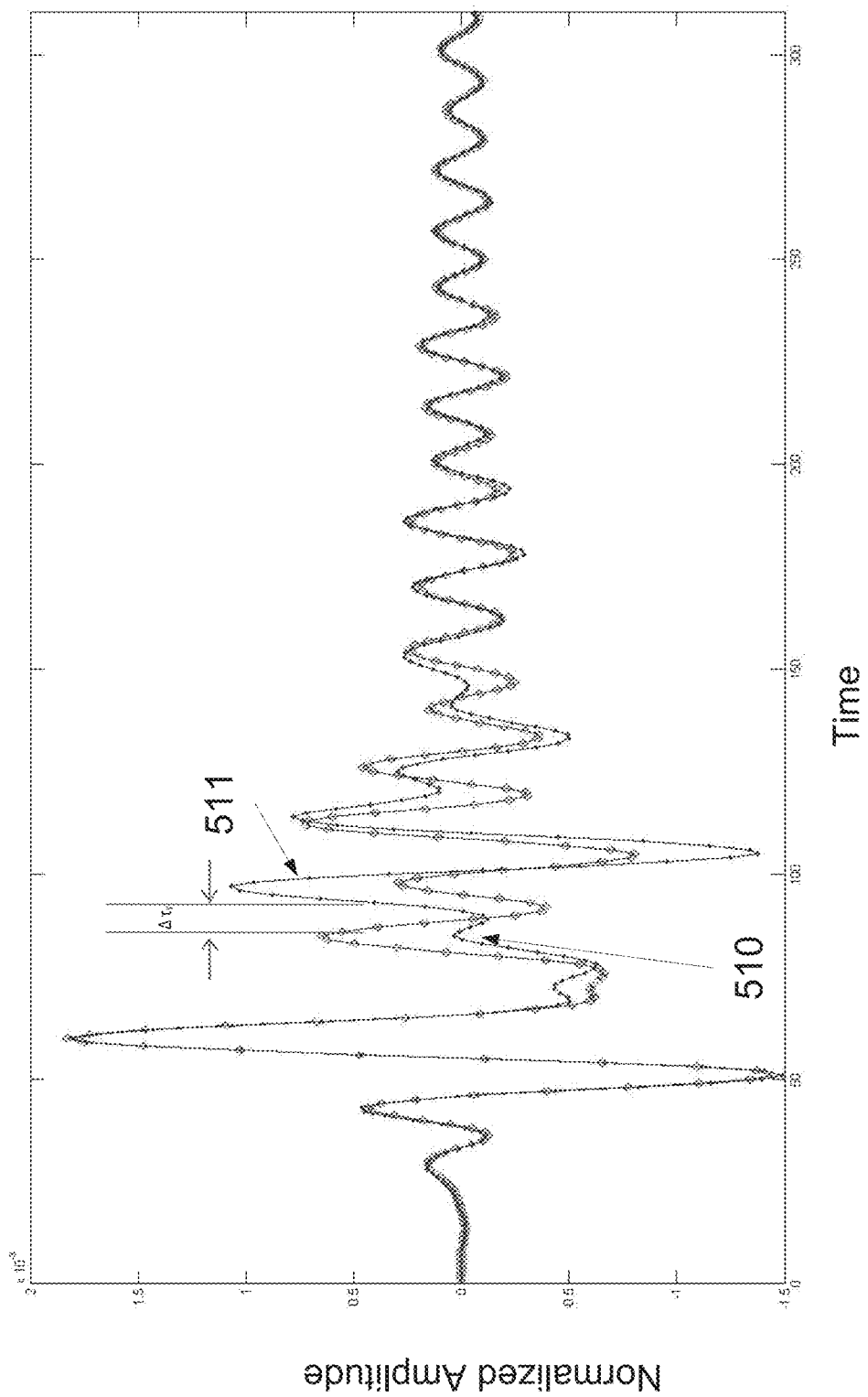
FIG. 2 is a graph two signals each based on EM reflections intercepted from an exemplary cardiac tissue of a patient, according to some embodiments of the present invention.

Reference is now also made to FIG. 2, which is a graph two signals 510, 511 each based on EM reflections intercepted from an exemplary cardiac tissue of a patient, by one of a transducer of a monitoring device, for example as described below in relation to FIG. 3, according to some embodiments of the present invention. Each signal is recorded during respective correlated periods $t_1$ and $t_2$. The correlation between the signals 510, 511 is performed to allow matching between EM reflections from a monitored area in the thorax of the patient in period $t_1$ and in period $t_2$. The matching allows detecting a local deviation between the signals 510, 511. As the EM reflections pattern from which the signals are reconstructed are affected by the mechanical properties of the cardiac tissue, such a local deviation is indicative of a mechanical property—a motion of the cardiac tissue. For example, the local deviation $\Delta\tau_x$, which is depicted in FIG. 2, is indicative of the motion of the boundary between the heart and the lung during the period between $t_1$ and $t_2$. In FIG. 2, $t_1$ is a systole and period $t_2$ is a diastole and therefore the $\Delta\tau_x$ reflects a motion occurring during the period between them, for example as an outcome of the heart contraction. The location of the local deviation along the signal is indicative of the location of the moving tissue. The location may be calculated according to the occurrence time (X axis) along the signal tracing. This time corresponds with the depth in the body of the patient, for example from the location of the sensor. In FIG. 2 a local deviation of 200 ps ($\Delta\tau y$) from approximately 0.6 to 0.8 nanoseconds from the first initial reflection which is equivalent to a deviation of 7.5 mm in depth of 25 mm, assuming the reflection from the heart is measured through the lung, whose real part of the dielectric coefficient is approximately 20. This local deviation is an outcome of the movement of the heart-lung boundary in 200 ms, corresponding approximately to the diastole and systole time.

Figure 7:
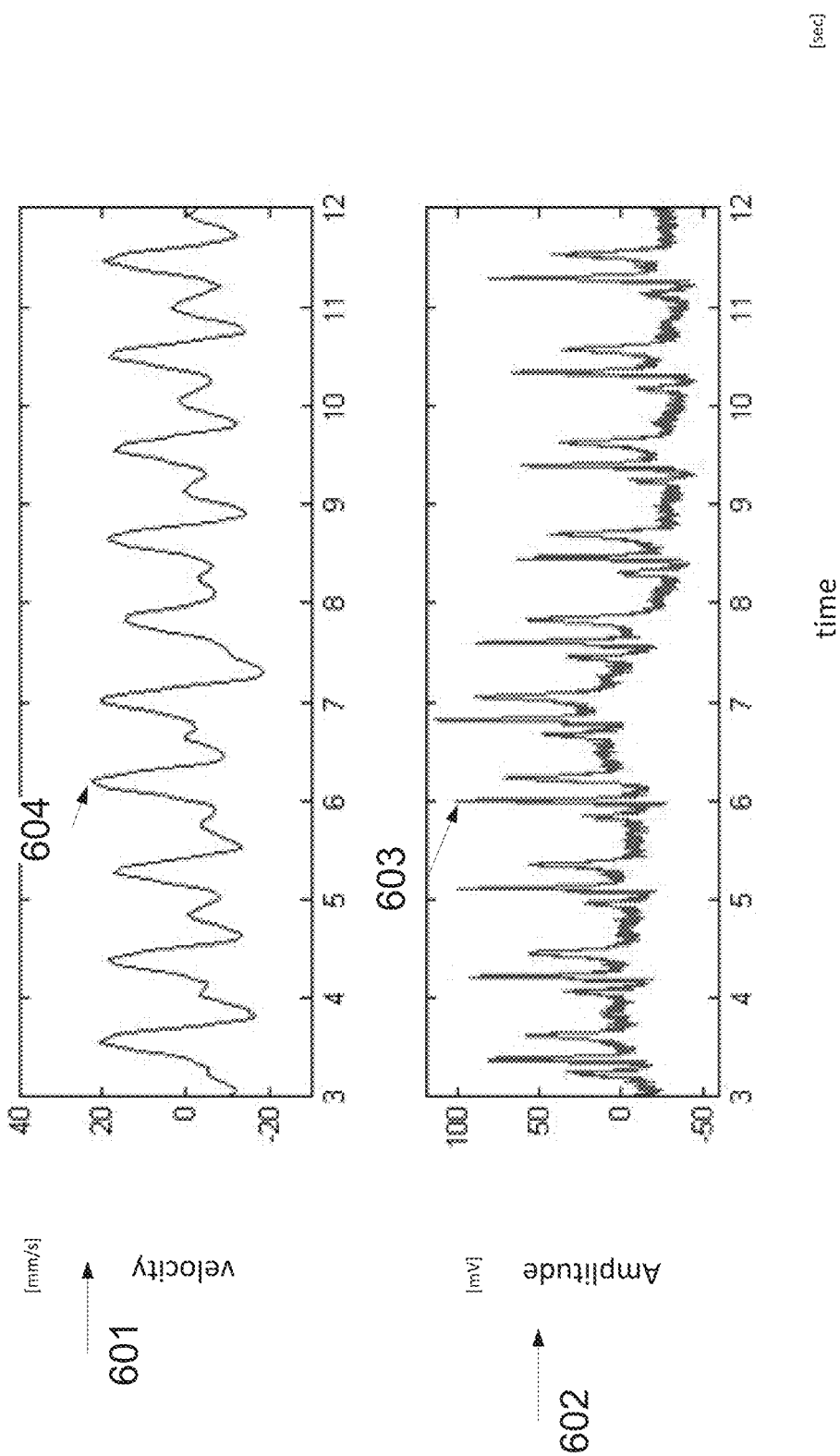
FIG. 7 is an illustration a cardiac tissue velocity graph and a respective cardioelectric tracing which are temporally synchronized and compared, according to some embodiments of the present invention.

Optionally, a mechanical property, such as the velocity of a cardiac tissue during a certain period, may be calculated by monitoring local deviations in a certain instant measured in relation to a reference instance, such as the instance of transmitting the EM radiation. The length of the local deviation corresponds with the velocity. By monitoring local deviations along the certain period, a mechanical tracing describing the velocity during that certain period may be calculated. For example, numeral 601 in FIG. 7 shows a graph that depicts the velocity of the boundary between the heart and the lung. The graph is based the local deviations which are monitored in a periodical instant which is indicative of reflections from the boundary between the heart and the lung.

Additionally or alternatively, the velocity of a certain cardiac tissue in a certain instance may be calculated by measuring the length of the local deviation and dividing it by the time period of this instance, which is indicative to the time it took the cardiac tissue to move so as to create the local deviation.

Additionally or alternatively, the velocity of a certain cardiac tissue is calculated by measuring the difference in the returned phase shift from transmission after adjusting to the wavelength. That could be done by transmitting and receiving a wave around one center frequency, or by using a wide pulse and computing a shift between the transmitted frequencies and intercepted frequencies. The adjusted measured shifts may be averaged to provide one corresponding robust estimation of the velocity, and\or any other mathematically operation, such as outlier exclusion by median operator and the like. Smoothing of the instant computed velocities may be conducted over time. As shown at 104, the mechanical tracing is analyzed. The analysis allows diagnosing and/or detecting physiological conditions, such as pathological cardiac conditions, for example by identifying a change or an indication of a change in relation to a normal motion pattern, a pulsation pattern, and/or any normal pattern of a mechanical behavior of a cardiac tissue, a number of contractions per cardiac cycle, a signal indicative of an irregular heart motion, an irregular cardiac cycle, an irregular heartbeat, an irregular relationship between a mechanical property during a cardiac cycle and additional data pertaining to the cardiac tissue, such as the cardioelectric tracing, during the same cardiac cycle. The change is analyzed so as to allow the identification of a change in one or more mechanical tracings of mechanical properties of the cardiac tissue, for example, its movement and/or contractility.

Optionally, the analysis is of a mechanical tracing that is indicative of the velocity of the motion and/or the pulsation of the heart or aorta, optionally by computing one or more spatial vectors in a monitoring period. In such a manner, a deviation from a normal motion and/or pulsation pattern and/or a pathological trend which lasts during few hours and/or days may be detected by extracting and classifying a motion pattern from the spatial vectors.

Optionally, a motion vector, which is calculated according to outputs of one or more transducers, may be calculated during the analysis so as to assess a cardiac performance.

As described above, the velocity of a certain cardiac tissue may be calculated. This allows calculating a clinical indication, such as the acceleration of the cardiac tissue, which is indicative of a ventricular pressure change over time (dp/dt). Optionally, the clinical indication is analyzed, in real time, for example by matching it with one or more expected normal values, ranges, and or patterns which are locally hosted by the monitoring device. In such embodiments the monitoring device may alarm a user and/or a medical center about abnormal clinical indications, optionally in real time, for example as described below.

Additionally or alternatively, the monitoring of the velocity of a certain cardiac tissue for a long period, such as hours and/or days, allows detecting pathological trends, for example a continuous slow down in the velocity and/or acceleration of the cardiac tissue due to ischemic processes, pericardial effusion, valvular deficiencies and the like.

Additionally or alternatively, the analysis of the mechanical tracing allows calculating a mechanical property such as the duration of a heart contraction. This may be done by calculating the time period between a first instance in which the first cardiac tissue contracts and a second instance in which the mechanical tracing indicates that one or more cardiac tissues, such as the ventricles, are relaxing. The analysis of such a mechanical property allows diagnosing and/or detecting a pathological cardiac condition, such as an elevated afterload, lack of intra and/or inter-ventricular synchronous contraction, either due to abnormal electrical activation pattern and/or due to an abnormal myocytes contraction. The analysis of such a mechanical property further allows diagnosing and/or detecting pathological conditions such as ischemic processes, presence and/or an absence of infracted regions in the myocardium or abnormal activation pathways due to left or right bundle branch blocks, Wolff-Parkinson-White (WPW) syndrome, a presence and/or an absence of ectopic foci, and/or decreased presence of critical substances such as calcium.

Additionally or alternatively, the analysis of the mechanical tracing allows estimating a mechanical property such as acceleration of a cardiac tissue along a cardiac cycle and optionally, the acceleration peak, which is estimated to be correlated with a heart ejection, and more particularly with a change of ventricular pressure during the cardiac cycle. The analysis of such a mechanical property allows diagnosing and/or detecting a pathological cardiac condition such as valvular deficiencies, for example mitral regurgitation.

If the analysis does not indicate a pathological cardiac condition, such as arrhythmia and hypertrophy, for example by identifying a change in the pattern of the motion and/or pulsation of the cardiac tissue and/or a deviation from a certain range of values, the process is repeated, as shown at 105. Else, as shown at 106 an alarm, a report and/or any other message that is indicative of the change and/or the deviation is outputted, for example presented and/or forwarded as described below. The system may report the current measurement and the analysis of the current clinical status.

Additionally or alternatively, the transmission sessions allow monitoring one or more values of one or more dielectric properties of the cardiac tissue and detecting a deviation of these values from predefined thresholds and/or ranges, for example similar to the described in International Patent Applications Numbers IL2008/001198 and/or IL2008/001199, filed on Sep. 4, 2008, which are incorporated herein by reference. In such a manner, pathological conditions such as pericardial effusion may be detected. In pericardial effusion, the space between the pericardium and myocardium is filled slowly or rapidly with blood, limiting the filling of the heart with blood, and risking for severe malfunction and death. Such a monitoring may provide an early detection for providing a more efficient treatment. According to some embodiments of the present invention, the transmission sessions allow diagnosing and/or detecting pathological cardiac conditions by matching mechanical tracings with a biomechanical model, optionally temporal. Optionally, the biomechanical model defines governing biomechanical equations and/or a parameterization of anatomical tissues based on parameter reconstruction. Optionally, the biomechanical model is based on anatomical/mechanical models using information that may be provided by one or more imaging modalities, such as echocardiograms, CT or MRI. Optionally, the biomechanical model defines an estimation of a number of physiological states of the heart during a period. Optionally, the biomechanical model of the tissue layers describes, both spatially and temporally, periodic effects of the respiration and the heart beat cycles and expected deviations according to various physiological phenomenon, for example various respiration patterns, such as cheyne stokes respiration pattern. In such a manner, a match to a physiological state may be indicative of a potential pathological condition.

Optionally, the monitoring and/or detecting is adjusted to take into account changes in the dielectric related properties of the monitored cardiac tissue, such as changes which occur as an outcome of a reaction to a medical treatment, a change of physiological state and body movements. Optionally, the transmission, receiving and optionally the analysis of the received reflections are performed by a wearable monitoring device, a probe and/or by a device having wearable probes, for example similar to the devices which are described in International Patent Applications Numbers IL2008/001198 and/or IL2008/001199, filed on Sep. 4, 2008, which are incorporated herein by reference. For brevity, each one of these devices may be referred to herein as a monitoring device or a probe.

As outlined above, one or more mechanical tracings of the cardiac tissue may be generated by intercepting and analyzing the EM reflections from one or more cardiac tissues during a period. Optionally, additional signs, which may provide meaningful clinical data as a complement to a clinical picture, are computed according to the EM properties. Such additional signs may include a respiratory rate and depth and/or an accumulation and/or dispersion of fluid within the cardiac and pulmonary tissues as well as of other chest fluids such as pleural effusion.

As outlined above, the method is optionally designed for long monitoring periods of 6 hours or more, for example as further described below. As such, the analysis may be adjusted to take into account changes in the dielectric related properties of the monitored cardiac tissue, such as changes, which occur as an outcome of thoracic movements, and other body movements.

Optionally, the analyzed data is presented to the patient and/or a medical caregiver and/or transferred to a central medical server, for example as described below. For example, mechanical tracings and/or alarms may be forwarded to an emergency center of a proximate hospital and to a central medical center.

According to some embodiments of the present invention, several types of sensors are used for monitoring the cardiac tissues. In such a manner, the reflections of the EM radiation may be analyzed together with signals from other modalities, such as an ultrasound modality that outputs a movement estimation of a cardiac tissue, which is optionally another cardiac tissue, and a pulse oximeter that outputs the blood saturation of the patient.

For example, ultrasound modality provides high tissue penetration ability when it comes to tissues rich with fluids while presenting less contrast between fat and muscles, for example dielectric coefficients are around 60 for a muscle tissue and 5 for a fat tissue, while the acoustic impedances differs only by few percent.

Optionally, the mechanical tracing is registered, calibrated, verified and/or otherwise adjusted according to the motion of another tissue, for example according to outputs of an additional sensor, such as an ultrasound sensor and/or an accelerometer which is placed on or in proximity to the tissue. Optionally, the mechanical tracing is registered according to outputs of a tiltmeter and/or accelerometer, which are indicative of the activity level of the patient. Optionally, the mechanical tracing is adjusted in a specific time instance according to the mechanical tracing of other sensors which is placed on or in proximity to the traced cardiac tissue, for example an ultrasound sensor and/or the aforementioned tiltmeter and/or accelerometer. Optionally, the mechanical tracing of a specific cardiac tissue for example the left ventricle is adjusted according to the mechanical tracing of another specific cardiac tissue, for example according to traced motion of the left ventricle.

Optionally, a plurality of RF transducers are used for assessing the movement of the heart from one or more angles and providing a number of spatial vectors that characterize the heart motion. Optionally, one or more of the RF transducers are placed to monitor the heart through the lungs. In such a manner, a relatively high dielectric contrast is provided at the muscle lung edge.

Optionally, the plurality of RF transducers allows monitoring mechanical properties of different cardiac tissues simultaneously. In such an embodiment, each RF transducer may intercept EM reflections from a different cardiac tissue, allowing the calculation of different mechanical tracings for different cardiac tissues. The mechanical tracings, which optionally document mechanical properties during a common period, may be correlated and matched to estimate a synchrony between different cardiac tissues, for example the contractions synchrony of two cardiac tissues, such as the left and the right ventricular chambers. This may be calculated by matching multiple peaks which are detected in a common cardiac cycle and/or directly measuring a mechanical onset of the contractions of each tissue.

Additionally or alternatively, the method described hereinabove may be executed in parallel to other monitoring methods such as monitoring of the congestion levels of the lungs.

Additionally or alternatively, the outputs of an accelerometer that is positioned on the chest may be used for registering the intercepted radiation, for example as described in International Patent Applications Numbers IL2008/001198 and/or IL2008/001199, filed on Sep. 4, 2008, which are incorporated herein by reference. Such a registration allows providing a finer accuracy in tracking heart motion overcoming chest motion and vibrations.

Figure 3:
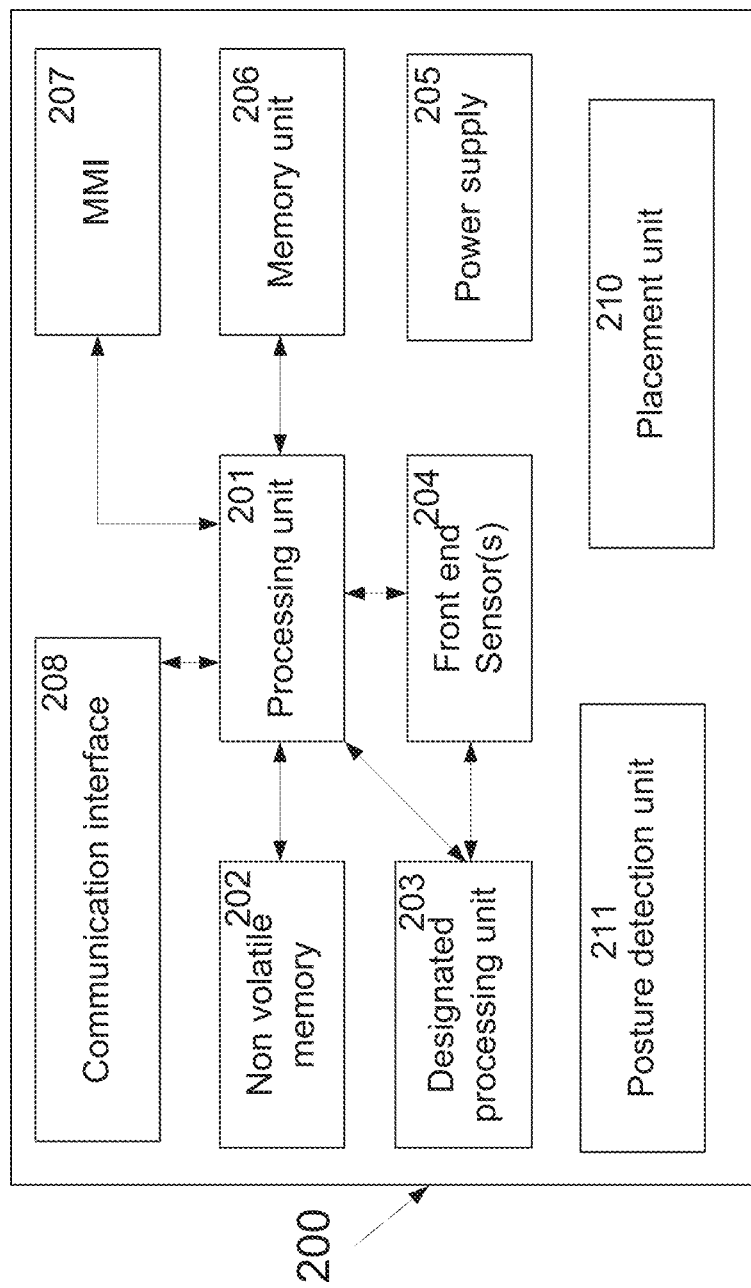
FIG. 3 is a schematic illustration of an exemplary monitoring device, according to some embodiments of the present invention.

Reference is now also made to FIG. 3, which is a schematic illustration of an exemplary monitoring device 200, according to some embodiments of the present invention. Optionally, the exemplary monitoring device 200 is designed as a wearable and/or as a stationary monitoring device, for example as described in International Patent Applications Numbers IL2008/001198 and IL2008/001199, filed on Sep. 4, 2008, which are incorporated herein by reference. The monitoring device 200 may be used for implementing any of the aforementioned methods.

The exemplary device 200 comprises a central processing unit (CPU) and/or a digital signal processing (DSP) which may be referred to herein as a processing unit 201. Optionally, the processing unit 201 runs a real-time operating system (RTOS) that is responsible for coordinating all functions of the monitoring device 200. The processing unit 201 is optionally used for analyzing the outputs of the one or more front-end sensors 204 which are described below. Optionally, the one or more front-end sensors 204 are ECG electrodes. Optionally, the one or more front-end sensors 204 capture signals which are forwarded to the processing unit 201 that calculates a deviation from a motion pattern of the cardiac tissue. The deviation analyzed from the reflected signals may be used for detecting a pathological pattern. For example, the processing unit 201 may compare between the deviation and a set of one or more predefined values. The data that is calculated by the processing unit 201 is optionally used for generating one or more alerts and/or notifications. It should be noted that the term processing unit means a local processing unit, a distributed processing unit, and/or a remote processing unit which is used for performing the functioning of the processing unit that is described herein. In an embodiment in which the processing unit is remote, the data that is forwarded to the processing unit is transmitted for remote processing by the remote processing unit.

The monitoring device 200 further comprises a memory unit 202, such as a non volatile memory, that is designed for storing the operating system and parameters which are needed for the functioning of the monitoring device 200. Optionally, the memory unit 202 is used for recording mechanical and electromechanical tracings and/or calculations which are based thereupon, for example as further described above. Such a recording allows examining changes in the motion pattern, optionally during a period that lasts between few hours and days. The recording allows calculating a repetitive pattern and/or the identification of a deviation from a normal range that is optionally adjusted according to the specific user. Optionally, the memory unit 202 is used for recording readings of medical sensors which are connected to the monitoring device 200 and/or embedded therein. Optionally, the memory unit 202 is used for storing additional information, such as application executables codes, configuration files for the processing unit 201, preset parameters, long term state parameters and tables. The memory unit 202 may be used for storing additional user related data, such as the patient identification information, version information, user specific thresholds, authentication and/or security keys.

The monitoring device 200 further comprises a rapid access volatile memory unit 206, such as a dynamic random access memory (DRAM), a synchronous DRAM (SDRAM), and/or any other volatile memory for storing data that is needed to be accessed in a limited time for short terms. It may be interfaced by the processing unit 201, the below mentioned designated IC and/or any other component of the monitoring device 200.

Optionally, the monitoring device 200 comprises a designated processing unit 203, such as a designated integrated circuit (IC), for example an application-specific integrated circuit (ASIC) or a field-programmable gate array (FPGA) that contains logic blocks and programmable interconnects which are programmed to implement some of the functions required to process the data from the sensors front-ends. The designated processing unit 203 communicates with the processing unit 201, the memory unit 202, and/or with other components of the device for various tasks. Additionally or alternatively, the designated processing unit 203 may also implement any of the other blocks as an integrative solution. For example, the FPGA or ASIC may incorporate the processing unit 101 and/or another processing unit. Optionally, the logic blocks are programmed to implement monitoring methods as described above.

The hardware may be used for processing measurements obtained from other modalities such as oxygen saturation or ECG measurements.

As described above and depicted in FIG. 3, the monitoring 200 further comprises one or more probes, such as front-end sensors 204, for example EM transceivers, for transmitting a plurality of electromagnetic (EM) waves toward the thorax of the patient and for capturing reflections thereof from the cardiac tissues. In some embodiment, the beam is transmitted in a desired pulse and allows the capturing of a reflection thereof from various areas on the surface of the user's body. Optionally, the capturing is adjusted according to a selected operational mode, for example according to a selected swept frequency, a selected frequency hopping chirp, and a selected multiple carriers and the like. Other modes and/or gating patterns according to which the beam is transmitted and allows the capturing thereof are described in International Patent Applications Numbers IL2008/001198 and IL2008/001199, filed on Sep. 4, 2008, which are incorporated herein by reference.

Optionally, the monitoring device 200 is adjusted for long term usage, for example in terms of power consumption and heat dissipation, for example similar to devices which are described in International Patent Applications Numbers IL2008/001198 and/or IL2008/001199, filed on Sep. 4, 2008, which are incorporated herein by reference.

Optionally, the monitoring device 200 fits in a small form factor (SFF) housing which is adjusted for ambulatory patients, for example similar to devices which are described in International Patent Applications Numbers IL2008/001198 and/or IL2008/001199, filed on Sep. 4, 2008, which are incorporated herein by reference.

Optionally, the monitoring device 200 may be adjusted to facilitate easy replacement of disposable parts, such as batteries and padding, for example similar to devices which are described in International Patent Applications Numbers IL2008/001198 and/or IL2008/001199, filed on Sep. 4, 2008, which are incorporated herein by reference.

Optionally, the monitoring device 200 includes a placement unit 210 having a disengagement detector which examines the quality of measurement and optionally alert when improper positioning of the device 200 is detected, for example similar to placement units 210 which are described in International Patent Application Number IL2008/001199, filed on Sep. 4, 2008, which is incorporated herein by reference.

Optionally, front end sensors 204 comprise one or more medical sensors for capturing vital signs and/or other medical measures, for example an ECG sensor, a temperature sensor, a blood pressure transducer, a fluid rate recording transducer, and an echo-cardiographic sensor. The output of these sensors is forwarded to the processing unit 201 so as to allow a more accurate characterization of a dynamic heart function based on a plurality of measurements from a plurality of sensors. The medical sensors are either incorporated within the monitoring device and/or communicate therewith.

Figure 4:
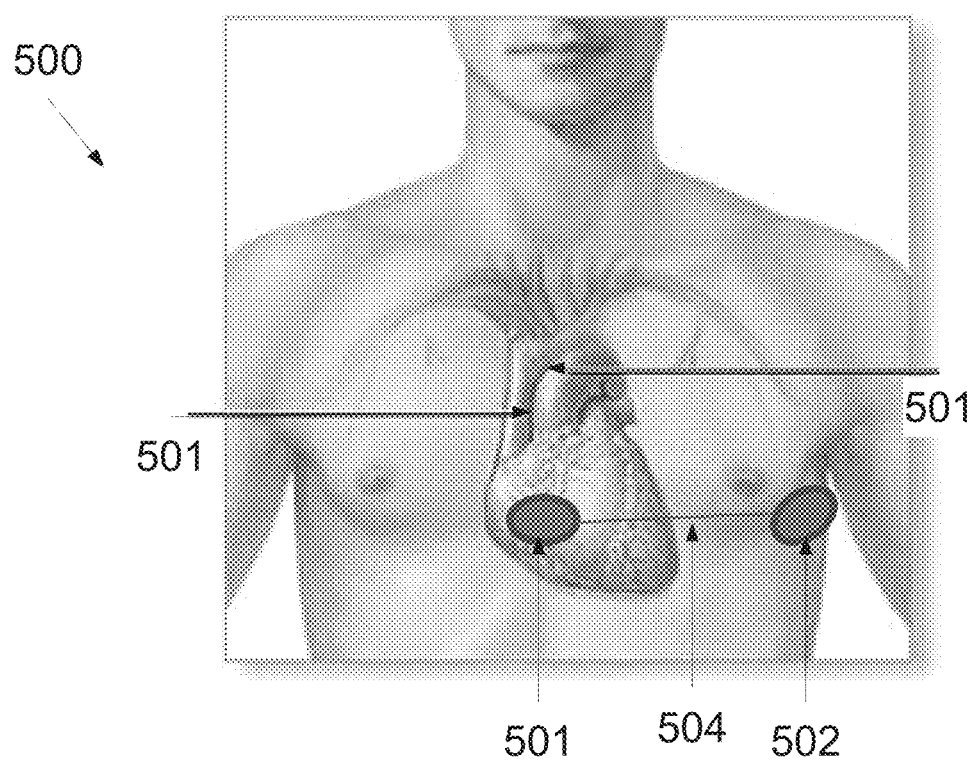
FIG. 4 is a schematic illustration of the thorax of an exemplary patient and sensor locations in which the RF transceivers and/or cardioelectric leads are placed, according to some embodiments of the present invention.

According to some embodiments of the present invention, a plurality of transducers are used. For clarity, reference is now also made to FIG. 4, which is a schematic illustration of the thorax of an exemplary patient 501 and sensor locations 502, 503 in which the RF transceivers and/or cardioelectric leads are placed, according to some embodiments of the present invention. For example, a first RF transducer 501 is placed on the front of the thorax, in front of the heart, capable of sensing motion and other mechanic properties in specific heart regions. A second RF transducer may be placed in another location on the thorax, for example on between the arm and the thorax. In such a manner, the EM radiation is received in two orthogonal or substantially orthogonal locations. The use of multiple sensors may be used to assess movement of different locations within the heart so as to allow assessing a related 2D or 3D vector of motion of the entire heart. Any number of additional sensors may be added to improve the accuracy and/or robustness of the spatial vector. As each sensor monitors motion of the heart from a different direction, a spatial motion vector may be computed by combining two or more motion vectors each calculated according to information from a different subset of the multiple sensors. Additionally or alternatively, the motion of two different cardiac tissues may be monitored, for example the left and right ventricles. In such a manner, the synchrony of the contractions and/or any other mechanical relation between the different tissues may be evaluated according to the intercepted reflections. One or more of the sensors 501, 502 may be used independently in order to evaluate the entire heart motion resulting mainly from the ejection of the ventricles, namely the jet effect.

Optionally, the leads of an ECG sensor are integrated into the body of the monitoring device 200. Additionally or alternatively, the leads of the ECG sensor are connected by wire to the body of the monitoring device 200. In such an embodiment the user may place the leads in different location, optionally according to predefined instructions.

According to some embodiments of the present invention, the monitoring device 200 incorporates an ECG sensor or receives outputs of such an ECG sensor, optionally wirelessly. Optionally, the ECG sensor comprises a number of leads. Optionally, one or more electrodes are integrated into the device 200 and one or more electrodes are separated from the monitoring device 200 and communicate therewith, optionally wirelessly. Leads could be positioned similar to the positioning of regular chest leads. Optionally the leads and the monitoring unit are incorporated in a wearable chest strap. The processing unit 201 receives and analyses the output of the ECG sensor and the aforementioned EM transceivers.

Optionally, the monitoring apparatus 200 is connected to a power supply element circuitry 205 that is designed for generating and distributing the power supply that is required for the components of the monitoring apparatus 200. The power supply element circuitry 205 comprises one or more batteries, optionally rechargeable.

Optionally, the monitoring device 200 comprises a man-machine interface (MMI) 207 for presenting data, such as an alert, a notification, statistical data, a current reading of the one or more front-end sensors 204 or external modality to the user, the user's caretaker, and/or others as desired. The MMI 207 may comprise a liquid crystal display (LCD), a touch screen, a speaker, a tactile generator, a set of light emitting diodes (LEDs), and/or any other indicator that may be used for presenting alerts and/or notifications which are based on a combination of the analysis of the mechanical tracings which are based on EM waves from an internal area in the body of the user, such as the cardiac tissues, and indicative of mechanical properties.
Optionally, the MMI 207 is separate and remote from the monitoring device and connected to it optionally using wired, wireless, and/or using a computer or communication network.
Optionally, the configuration of the wearable monitoring apparatus 200 may allow the patient and/or a caretaker to define which alarm to present and to whom, for example whether the alarm is visual, audible, and/or tactile.

Optionally, the monitoring apparatus 200 comprises a posture detection unit 211 for using EM radiation for detecting a posture of a user, for example as described in International Patent Application Number IL2008/001199, filed on Sep. 4, 2008, which is incorporated herein by reference. The posture affects the thickness of layers of tissues in the path to the heart, for example when a person lies on his side his heart tends towards that side and less pulmonary tissue resides on the path from the chest surface to the heart. As the reflection is influenced by the layers between the chest surface and the heart and the propagation time is accordingly affected, the analysis of the intercepted data may be adjusted according to the outputs of the posture detection unit 211. In such a manner the effect of the posture is reduced and/or eliminated.

According to some embodiments of the present invention, the monitoring device 200 is used for computing an electromechanical delay in real time. In such an embodiment, the cardioelectric tracing and the mechanical tracing are combined in real time to provide a real time feedback for cardiac therapies, such as cardiac resynchronization therapy (CRT). In such an embodiment, a caretaker may receive a real time feedback on the efficacy of the therapy she provides and/or a real time indication about the responsiveness of a cardiac tissue to a therapeutic procedure. For example, the monitoring device 200 may be used for identifying the optimal location of leads in a CRT implantation procedure. In particular, a CRT device may have a number of leads, for example one in the right ventricle to stimulate the septum, and another inserted through the coronary sinus to pace the lateral wall of the left ventricle. Often, for patients in normal sinus rhythm, there is also a lead in the right atrium to facilitate synchrony with the atrial contraction. The leads are designed for timing between the atrial and ventricular contractions, as well as between the septal and lateral walls of the left ventricle. By monitoring the efficacy of the leads in different location on the heart, the monitoring device 200 may be used to identify the locations in which the leads achieve optimal cardiac function, see McWilliam J A (1889). "Electrical stimulation of the heart in man" Br Med J 1: 348-50. doi:10.1136/bmj.1.1468.348. Partial quote in "Electrical Stimulation of the Heart in Man—1889", Heart Rhythm Society, Accessed May 11, 2007; Lidwell M C, "Cardiac Disease in Relation to Anaesthesia" in Transactions of the Third Session, Australasian Medical Congress, Sydney, Australia, Sep. 2-7 1929, p 160; and ^ a b Mond H, Sloman J, Edwards R (1982). "The first pacemaker". Pacing and clinical electrophysiology: PACE 5 (2): 278-82. doi: 10.1111/j.1540-8159.1982.tb02226.x. PMID 6176970 which are incorporated herein by reference.

Additionally or alternatively, the device may be used for monitoring the functionality and efficacy of a CRT and/or any other pacemaker, after the implantation of the leads. In such an embodiment, the monitoring device 200 may be provided after surgery to monitor the integration of the pacemaker and its functionality, optionally during different activities and/or situations of the patient.

Figure 5:
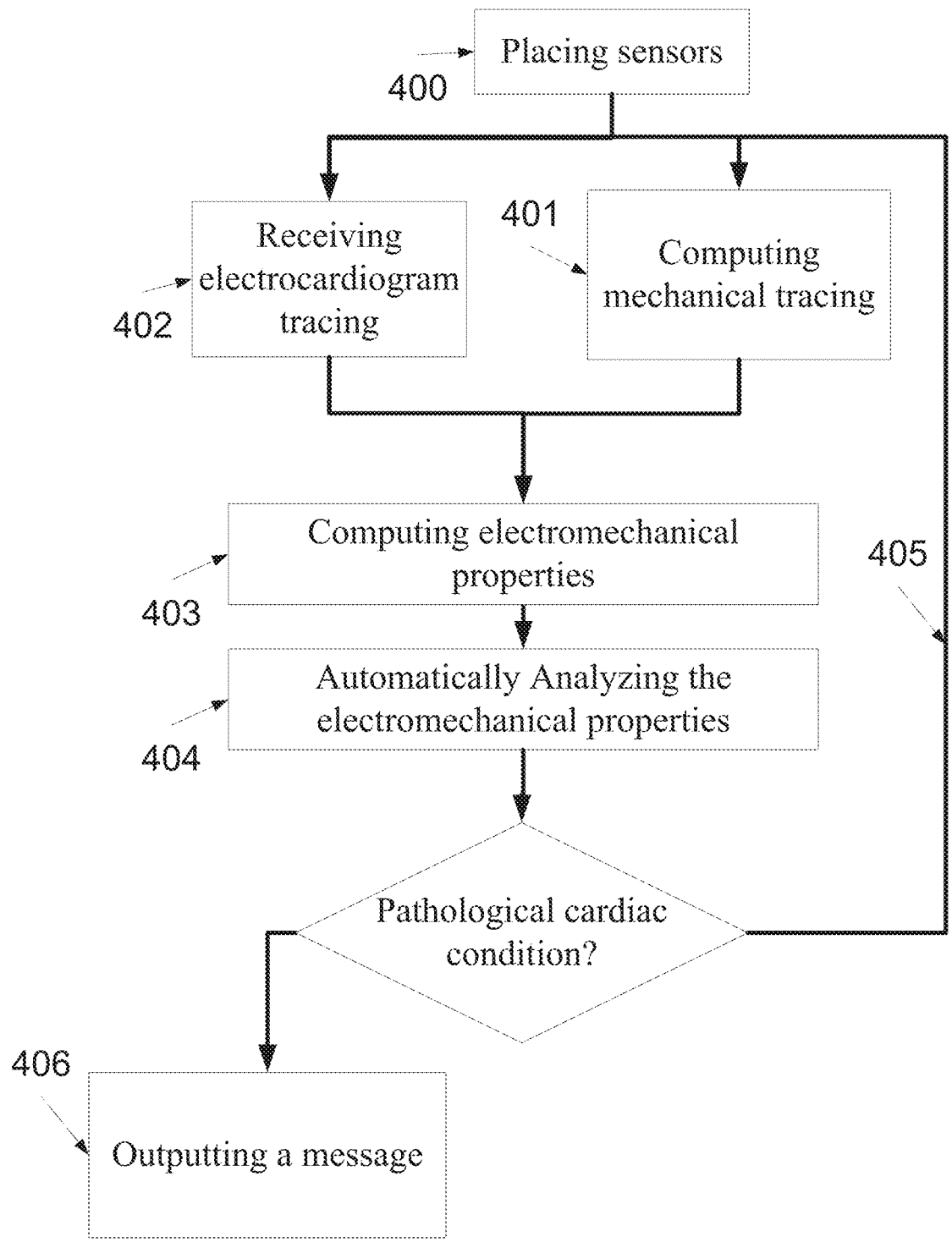
FIG. 5 is a flowchart of a method of monitoring one or more electromechanical properties, according to some embodiments of the present invention.

Reference is now also made to FIG. 5, which is a flowchart of a method of monitoring one or more electromechanical properties, according to some embodiments of the present invention.

First, in 400, EM and ECG sensors, optionally similar to the described above, are attached to the thorax of the patient 501. For clarity, reference is now also made, once again, to FIG. 4. Optionally, leads of an ECG sensor are placed in one or more of the sensor locations 502, 503. Optionally, an electrical conductor 504 is used to reference the measured potentials between the different leads.
As shown in 401, one or more mechanical tracing are computed, for example as described above, according to EM radiation which is reflected from a monitored cardiac tissue of a patient. As described above, the EM reflections allow generating one or more mechanical tracings. As shown in 402, cardioelectric tracing of the patient are simultaneously, or substantially simultaneously, received from a cardioelectric sensor, such as an ECG sensor. As used herein, a cardioelectric tracing means a measurement of the electrical pulses given off by one or more cardiac tissues during a period, such as an electrocardiograph record, electrocardiogram tracing, and the like.

Figure 6:
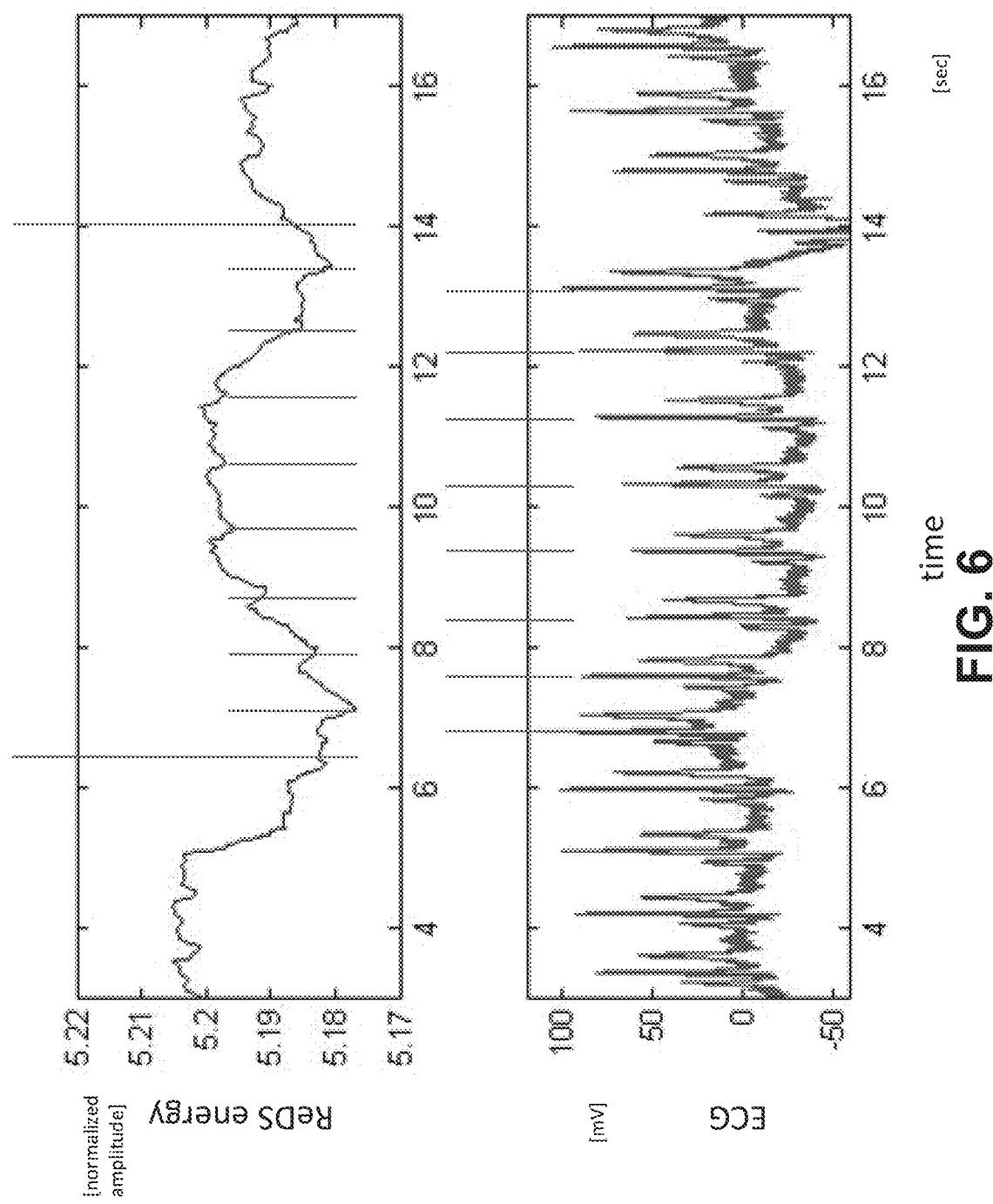
FIG. 6 is an illustration of two exemplary graphs, one depicting a signal which is based on EM reflections intercepted by a transducer and an electrical signal according to some embodiments of the present invention.

For example, reference is now made to FIG. 6, which includes a set of two exemplary graphs, one depicting a signal that is based on EM reflections intercepted by a transducer of the monitoring device depicted in FIG. 3 during a period t and a signal that is based on a cardioelectric value measured by a cardioelectric sensor, such as a ECG sensor during t, according to some embodiments of the present invention.

In the EM signal graph, the long vertical lines depict an instance which has been identified as an initiation of a respiration cycle during t, and the short vertical lines depicting heart beats. In the ECG signal graph, the solid lines are indicative of electrical onsets of an electrical activation (R). The EM signal graph depicts the energy of the reflected signal normalized to the transmitted energy and coordinated with the ECG signal on t.

Subsequently, as shown in 403, the outputs from 401 and 402 are used to compute one or more electromechanical properties of the monitored cardiac tissue. Optionally, 403 comprises temporally correlating between the cardioelectric tracing and the mechanical tracing. Optionally, the electromechanical properties include the electromechanical relationship between the cardioelectric tracing and the mechanical cardiac cycle, for example an electromechanical relationship between a QT interval of the cardioelectric tracing and the length of a respective mechanical cardiac cycle. Optionally, the electromechanical properties include the electromechanical relationship between amplitude changes and cardiac mechanical function changes.

Now, as shown at 404, the electromechanical properties are automatically analyzed so as to allow the detection of a physiological condition, such as a pathological cardiac condition, for example by the processing unit 201 of the monitoring device 200, Optionally, the electromechanical properties include an electromechanical delay in one or more cardiac cycles. The electromechanical delay reflects the delay between the electrical stimulation of the myocytes and the development of a muscle tension. The delay is the period between the electric onset of a cardiac cycle, which may be detected by analyzing the received cardioelectric tracing and the mechanical onset of the cardiac cycle, which may be detected by analyzing the received EM reflections. The electromechanical delay may be determined by calculating the period between the electrical activation, which at the peak of the R wave in the QRS complex of the cardioelectric tracing and the respective mechanical activation, which may be determined by detecting peak acceleration. If the electromechanical relationship between the onsets is indicative of electrical activation pattern of the ventricle, a pathological condition, such as bundle branch block, left and\or right, and\or WPW syndrome may be identified.

Multiple electromechanical delays may be computed between any detected specific pattern in an ECG signal and in a motion vector. For example, an electromechanical delay may be detected by identifying the P and/or T wave in the ECG signal and associating it with a peak of acceleration and\or the velocity of a motion vector that appears in a heart cycle that is associated with a contraction of another cardiac tissue such as the atriums and the ventricles.

For example, FIG. 7 depicts an illustration of a cardiac tissue velocity graph and a respective cardioelectric tracing which are temporally correlated, according to some embodiments of the present invention. Such a correlation allows monitoring the period between the electrical activation and a respective mechanical activation that is triggered by it, for example as shown by numerals 603 and 604.

Optionally, the electromechanical properties include the number of contractions per cardiac cycle. The cardioelectric tracing, which is a transthoracic interpretation of the electrical activity of the heart, indicates the beginning and the end of a cardiac cycle. The calculation of the motion of the cardiac tissue allows estimating the number of contractions which are performed per cardiac cycle. In such a manner, multiple contractions per cycle may be detected, indicating an asynchronous mechanical contraction of the left and/or the right side of the heart.

Optionally, the electromechanical properties may indicate asynchronous contraction which may be a result of abnormal electrical activation sequence or abnormal regional contraction response. The electromechanical parameter, could be compared with an estimation of the electrical activation synchrony as assessed from the ECG and appeared generally by wider QRS complex. Thus, it is possible to ascertain a diagnosis of abnormal electrical activation pattern, or in case of normal QRS complex to diagnose an abnormal contraction.

By continually, periodically, and/or randomly, repeating 401-404, as shown at 405, the electromechanical properties of the patient may be monitored during a period of more than 6 hours, for example 24 hours, similarly to the aforementioned monitoring period.

As shown at 406, when the analysis performed in 404 indicates a physiological condition, for example a pathological cardiac condition, such as relating to the aforementioned electromechanical delay optionally a delay that is longer than a predefined threshold, an alarm, a notice, and/or any other message is outputted and optionally presented to the patient and/or forwarded to a caretaker and/or medical center. Such a delay may be indicative of a pathological viability of the myocardium and/or the pumping efficiency of the patient's heart. In such a manner, the alarm may assist in detecting and/or predicting a malfunction as well as monitoring therapeutic procedure effects. As shown at 405, if no pathological condition is detected, the process is repeated so as to allow a continuous, periodical, and/or random monitoring of the electrometrical properties of the patient.

Optionally, the assessment of mechanical and/or electromechanical properties may be used to improve sensitivity and/or specificity of other modalities, to detect different pathological patterns, and as a complement to a clinical status assessment, as well as to provide a combined index with a clinical value. For example, such a combined index may be used for providing feedback to therapies such as medication. Similarly, it may be used to provide feedback to therapeutic procedures such as cardiac resynchronization therapy (CRT) in real time. Furthermore, the combined index may be used for positioning the resynchronization electrodes.

Reference is now made, once again, to FIG. 3. Optionally, the monitoring device 200 includes a communication interface 208 that allows forwarding data pertaining to the monitored electromechanical and/or mechanical properties to an external computing unit in an autonomous manner, for example similar to devices which are described in International Patent Applications Numbers IL2008/001198 and/or IL2008/001199, filed on Sep. 4, 2008, which are incorporated herein by reference. Optionally, the data is an alert that is forwarded to a monitoring center and/or a caretaker when hazardous scenarios are detected. Optionally, the monitored data is forwarded as is to the external computing monitoring device. In such embodiments, the external monitoring device performs the analysis and output a report, an alarm, and/or any other indication based thereupon. The analysis may be separated such that different processing units perform different processing stages.

Optionally, the transmission sessions are intermittently performed so as to reduce the power consumption. For example, the number of transmission sessions may be reduced when the patient is asleep and increased when the patient performs an intense physical activity. In such an embodiment, the transmission sessions may be dynamically changed according to a vital sign either estimated based on the intercepted EM radiation and/or a signal which is based thereupon or an external sensor, such as an accelerometer that is designed to measure the activity level of the patient and/or according to changes in the motion pattern of the cardiac tissue and/or reception of other sensors which are connected to the monitoring device 200.

It is expected that during the life of a patent maturing from this application many relevant devices and methods will be developed and the scope of the term EM radiation, EM reflections, a power source, and a communication unit is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for monitoring at least one cardiac tissue, comprising:
   intercepting a plurality of reflections of an electromagnetic (EM) radiation reflected from at least one cardiac tissue of a patient in a plurality of EM radiation sessions;
   computing a mechanical tracing indicative of at least one mechanical property of said at least one cardiac tissue according to said plurality of reflections;
   receiving a cardioelectric tracing;
   determining an electromechanical property by combining said mechanical tracing and said cardioelectric tracing, wherein said electromechanical property includes a number of contractions performed per cardiac cycle;
   analyzing said electromechanical property so as to detect a presence or an absence of a physiological condition; and
   outputting said analysis.

2. The method of claim 1, wherein said intercepting is performed during a period of at least 6 hours.

3. The method of claim 1, wherein said mechanical property comprises a member of a group consisting of motion velocity, motion acceleration, contractility, a length of a heart contraction and a pulsation.

4. The method of claim 1, wherein said computing comprises calculating a velocity of said at least one cardiac tissue according to a local deviation between signals generated according to EM reflections in first and second periods.

5. The method of claim 1, wherein said computing comprises registering said mechanical tracing according to a movement of at least one of said patient and an organ of said patient.

6. The method of claim 1, wherein said computing comprises adjusting said mechanical tracing according to a blood saturation level of said patient.

7. The method of claim 1, wherein said computing comprises adjusting said mechanical tracing according to a motion of an additional body tissue of said patient.

8. The method of claim 1, wherein said computing comprises registering said mechanical tracing according to a posture of said patient.

9. The method of claim 1, wherein said intercepting is performed during a period of at least 24 hours.

10. The method of claim 1, wherein said outputting comprises forwarding a notification indicative of said physiological condition to a remote medical center.

11. The method of claim 1, wherein said plurality of EM radiations are intermittently transmitted during a period selected according to at least one of an activity of said patient and a vital sign of said patient.

12. The method of claim 1, further comprising performing said intercepting and computing for an additional cardiac tissue to compute an additional mechanical tracing of at least one mechanical property of said at least one cardiac tissue and matching between said mechanical tracing and said additional mechanical tracing to estimate a synchrony between a contractility of said at least one cardiac tissue and a contractility of said additional cardiac tissue.

13. A method for monitoring at least one cardiac tissue, comprising:
   computing a mechanical tracing of at least one mechanical property of at least one cardiac tissue of a heart of a patient according to electromagnetic (EM) radiation reflected therefrom during a period;
   receiving a cardioelectric tracing generated by measuring an electrical activity of said heart during said period;
   combining said mechanical tracing and said cardioelectric tracing to determine an electromechanical property, wherein said electromechanical property includes a number of contractions performed per cardiac cycle;
   automatically analyzing said electromechanical property to detect a presence or an absence of a physiological condition during said period; and
   outputting said analysis.

14. The method of claim 13, wherein said period lasts at least 6 hours.

15. The method of claim 13, wherein said electromechanical property includes a delay between an electric activation and a contraction of said number of contractions.

16. The method of claim 13, wherein said electromechanical property includes a QT interval and a length of a cardiac cycle.

17. The method of claim 13, wherein said electromechanical property includes a value indicative of an amplitude change and a cardiac mechanical function change.

18. The method of claim 13, wherein said electromechanical property includes a value indicative of an amplitude change and a cardiac mechanical function change.

19. The method of claim 13, wherein said physiological condition indicates an asynchronous mechanical contraction of a left or right side of the heart.

20. The method of claim 13, wherein said physiological condition indicates an abnormal electrical activation sequence or an abnormal regional contraction response.

* * * * *